US012318080B2

(12) United States Patent
Swift et al.

(10) Patent No.: US 12,318,080 B2
(45) Date of Patent: Jun. 3, 2025

(54) ILLUMINATED SURGICAL RETRACTOR CAPABLE OF HAND-HELD OPERATION AND OF BEING MOUNTED TO A FIXED FRAME

(71) Applicant: CooperSurgical, Inc., Trumbull, CT (US)

(72) Inventors: Jason Swift, Newburyport, MA (US); Matthew Traub, Andover, MA (US); James Pehl, Methuen, MA (US)

(73) Assignee: CooperSurgical, Inc., Trumbull, CT (US)

( * ) Notice: Subject to any disclaimer, the term of this patent is extended or adjusted under 35 U.S.C. 154(b) by 0 days.

(21) Appl. No.: 18/450,881

(22) Filed: Aug. 16, 2023

(65) Prior Publication Data

US 2025/0025145 A1 Jan. 23, 2025

Related U.S. Application Data

(60) Provisional application No. 63/514,987, filed on Jul. 21, 2023.

(51) Int. Cl.
*A61B 17/02* (2006.01)
*A61B 90/35* (2016.01)

(52) U.S. Cl.
CPC .............. *A61B 17/02* (2013.01); *A61B 90/35* (2016.02); *A61B 2217/005* (2013.01)

(58) Field of Classification Search
CPC . A61B 17/02; A61B 17/0206; A61B 17/0218; A61B 90/35
See application file for complete search history.

(56) References Cited

U.S. PATENT DOCUMENTS

| | | | |
|---|---|---|---|
| 559,122 | A | 4/1896 | Daily |
| 659,182 | A | 10/1900 | Pilling |
| 2,235,979 | A | 3/1941 | Brown |
| 2,247,458 | A | 6/1941 | Shepard |
| 2,482,971 | A | 9/1949 | Golson |
| 2,592,190 | A | 4/1952 | Rubens et al. |
| 3,324,850 | A | 6/1967 | Gunning et al. |
| 3,332,414 | A | 7/1967 | Gasper |
| 3,532,088 | A | 10/1970 | Fiore |
| 3,592,199 | A | 7/1971 | Ostensen |
| 3,595,222 | A | 7/1971 | Vellacott |

(Continued)

FOREIGN PATENT DOCUMENTS

| | | |
|---|---|---|
| CN | 2239235 Y | 11/1996 |
| CN | 2265156 Y | 10/1997 |

(Continued)

OTHER PUBLICATIONS

International Search Report for International application No. PCT/US2016/016154 issued May 19, 2016 for corresponding U.S. application, U.S. Appl. No. 14/614,413.

(Continued)

*Primary Examiner* — Si Ming Ku
(74) *Attorney, Agent, or Firm* — Fish & Richardson P.C.

(57) ABSTRACT

A surgical retractor, comprising a handle, a blade extending from the handle, wherein the handle has an ergonomic construction configured for hand-held use of the retractor, and wherein the handle is configured to attach to one or more of a fixed frame and a fixed arm of a surgical positioning device.

30 Claims, 12 Drawing Sheets

(56) References Cited

U.S. PATENT DOCUMENTS 3,638,644 A 2/1972 Reick
3,650,266 A 3/1972 Pestka et al.
3,675,641 A 7/1972 Fiore
3,716,047 A 2/1973 Moore et al.
3,729,006 A 4/1973 Wilder et al.
3,762,400 A 10/1973 McDonald
3,769,968 A 11/1973 Blount et al.
3,789,835 A 2/1974 Whitman
3,815,585 A 6/1974 Fiore
3,826,248 A 7/1974 Gobels
3,851,642 A 12/1974 McDonald
3,934,578 A 1/1976 Heine
3,945,371 A 3/1976 Adelman
3,978,850 A 9/1976 Moore et al.
4,067,323 A 1/1978 Troutner
4,156,424 A 5/1979 Burgin
4,210,133 A 7/1980 Castaneda
4,226,228 A 10/1980 Shin et al.
4,263,899 A 4/1981 Burgin
4,300,541 A 11/1981 Burgin
4,337,763 A 7/1982 Petrassevich
4,432,351 A 2/1984 Hoary
4,492,220 A 1/1985 Hayes
4,502,468 A 3/1985 Burgin
4,527,553 A 7/1985 Upsher
4,546,761 A 10/1985 McCullough
4,551,129 A 11/1985 Coleman et al.
4,562,832 A 1/1986 Wilder
4,566,439 A 1/1986 Burgin
4,574,784 A 3/1986 Soloway
4,597,383 A 7/1986 Van Der Bel
4,607,623 A 8/1986 Bauman
4,619,248 A 10/1986 Walsh
4,638,792 A 1/1987 Burgin
4,759,349 A 7/1988 Betz et al.
4,766,887 A 8/1988 Cecil, Jr. et al.
4,807,600 A 2/1989 Hayes
4,884,559 A 12/1989 Collins
4,905,670 A 3/1990 Adair
4,934,352 A 6/1990 Sullivan, Jr.
4,971,036 A 11/1990 Collins
5,018,507 A 5/1991 Montaldi
5,026,368 A 6/1991 Adair
5,054,906 A 10/1991 Lyons, Jr.
5,063,908 A 11/1991 Collins
5,143,054 A 9/1992 Adair
5,165,387 A 11/1992 Woodson
5,174,278 A 12/1992 Babkow
5,179,937 A 1/1993 Lee
5,179,938 A 1/1993 Lonky
5,222,271 A 6/1993 Eganhouse
D337,384 S 7/1993 Schucman
5,231,973 A 8/1993 Dickie
5,318,009 A 6/1994 Robinson
5,329,938 A 7/1994 Lonky
5,427,152 A 6/1995 Weber
5,438,976 A 8/1995 Nash
5,465,709 A 11/1995 Dickie et al.
5,499,964 A 3/1996 Beck et al.
5,512,038 A 4/1996 O'Neal et al.
5,553,627 A 9/1996 Newkirk
5,695,492 A 12/1997 Brown
5,716,329 A 2/1998 Dieter
5,785,648 A 7/1998 Min
5,840,013 A 11/1998 Lee et al.
5,846,249 A 12/1998 Thompson
5,865,729 A 2/1999 Meehan
5,873,820 A 2/1999 Norell
5,879,304 A 3/1999 Schuchman et al.
5,888,195 A 3/1999 Schneider
5,899,854 A 5/1999 Slishman
5,902,315 A 5/1999 Dubois
5,916,150 A 6/1999 Sillman
5,967,971 A 10/1999 Bolser
6,001,077 A 12/1999 Ellman et al.
6,004,265 A 12/1999 Hsu et al.
6,036,638 A 3/2000 Nwawka
6,036,713 A 3/2000 Kieturakis
6,048,308 A 4/2000 Strong
6,080,105 A 6/2000 Spears
6,130,520 A 10/2000 Wawro et al.
6,176,824 B1 1/2001 Davis
6,186,944 B1 2/2001 Tsai
6,193,653 B1 2/2001 Evans et al.
6,217,512 B1 4/2001 Salo et al.
6,231,505 B1 5/2001 Martin
6,231,506 B1 5/2001 Hu et al.
6,254,247 B1 7/2001 Carson
6,277,067 B1 8/2001 Blair
6,319,199 B1 11/2001 Sheehan et al.
6,322,499 B1 * 11/2001 Evans .............. A61B 17/00008
600/245
6,346,085 B1 2/2002 Schiffman
6,359,644 B1 3/2002 Salvati
6,361,489 B1 3/2002 Tsai
6,363,763 B1 4/2002 Geringer et al.
6,379,296 B1 4/2002 Baggett
6,379,299 B1 4/2002 Borodulin et al.
6,394,111 B1 5/2002 Jacobs et al.
6,394,950 B1 5/2002 Weiss
6,413,208 B1 7/2002 Schöllhorn et al.
6,416,465 B2 7/2002 Brau
6,428,180 B1 8/2002 Karram et al.
6,432,045 B2 8/2002 Lemperle et al.
6,432,049 B1 8/2002 Banta
6,436,033 B2 8/2002 Tan
6,450,952 B1 9/2002 Rioux
6,468,206 B1 10/2002 Hipps et al.
6,468,232 B1 10/2002 Ashton-Miller et al.
6,487,440 B2 11/2002 Deckert et al.
6,504,985 B2 1/2003 Parker et al.
6,523,973 B2 2/2003 Galli
6,524,259 B2 2/2003 Baxter-Jones et al.
6,569,089 B1 5/2003 Covington et al.
6,569,091 B2 5/2003 Diokno et al.
6,589,168 B2 7/2003 Thompson
6,595,917 B2 7/2003 Nieto
6,616,603 B1 9/2003 Fontana
6,626,825 B2 9/2003 Tsai
6,663,576 B2 12/2003 Gombrich et al.
6,676,598 B2 1/2004 Rudischhauser et al.
6,719,688 B2 4/2004 Pecherer et al.
6,761,687 B1 7/2004 Doshi
6,830,547 B2 12/2004 Weiss
6,896,653 B1 5/2005 Vail, III et al.
7,014,340 B2 3/2006 Betis
7,029,439 B2 4/2006 Roberts et al.
D520,464 S 5/2006 Strong
7,223,223 B2 5/2007 Lindsay
7,276,025 B2 10/2007 Roberts et al.
7,306,559 B2 12/2007 Williams
7,474,820 B2 1/2009 Vayser et al.
7,492,116 B2 2/2009 Oleynikov et al.
7,510,524 B2 3/2009 Vayser et al.
7,631,981 B2 12/2009 Miller et al.
7,736,304 B2 6/2010 Pecherer
7,758,203 B2 7/2010 McMahon et al.
7,845,824 B2 12/2010 Robotham
7,878,973 B2 2/2011 Yee et al.
7,901,353 B2 3/2011 Vayser et al.
7,909,759 B2 3/2011 Pecherer
7,967,809 B2 6/2011 Jay-Robinson
8,012,089 B2 9/2011 Bayat
8,047,987 B2 11/2011 Grey et al.
8,052,702 B2 11/2011 Hess et al.
8,088,066 B2 1/2012 Grey et al.
8,096,945 B2 1/2012 Buchok et al.
8,142,352 B2 3/2012 Vivenzio et al.
8,142,353 B2 3/2012 Pecherer et al.
8,157,728 B2 4/2012 Danna et al.
8,162,824 B2 4/2012 Vayser et al.
8,162,826 B2 4/2012 Pecherer et al.
8,251,898 B2 8/2012 Pecherer
8,285,093 B2 10/2012 Vayser et al.

(56) References Cited

U.S. PATENT DOCUMENTS

| | | | |
|---|---|---|---|
| 8,292,805 | B2 | 10/2012 | Vayser et al. |
| 8,317,693 | B2 | 11/2012 | Grey et al. |
| 8,388,523 | B2 | 3/2013 | Vivenzio et al. |
| 8,394,017 | B2 | 3/2013 | Kieffer |
| 8,435,175 | B2 | 5/2013 | McMahon et al. |
| 8,459,844 | B2 | 6/2013 | Lia et al. |
| 8,512,234 | B2 | 8/2013 | Grey et al. |
| 8,512,237 | B2 | 8/2013 | Bastia |
| 8,555,892 | B2 | 10/2013 | Traub |
| 8,594,472 | B2 | 11/2013 | Vayser et al. |
| 8,596,847 | B2 | 12/2013 | Vayser et al. |
| 8,628,879 | B2 | 1/2014 | Pecherer et al. |
| 8,651,704 | B1 | 2/2014 | Gordin et al. |
| 8,708,896 | B2 | 4/2014 | Vayser et al. |
| 8,786,210 | B2 | 7/2014 | Delucia |
| 8,795,162 | B2 | 8/2014 | Vayser et al. |
| 8,821,385 | B2 | 9/2014 | Naito |
| 8,870,761 | B2 | 10/2014 | Vayser et al. |
| 8,890,489 | B2 | 11/2014 | Wood |
| D719,652 | S | 12/2014 | Swift |
| 8,899,809 | B2 | 12/2014 | Vayser et al. |
| 8,979,745 | B2 | 3/2015 | Swift |
| 9,002,159 | B2 | 4/2015 | Sutherland et al. |
| 9,005,115 | B2 | 4/2015 | Vayser |
| 9,044,161 | B2 | 6/2015 | Vayser et al. |
| 9,050,048 | B2 | 6/2015 | Nadershahi |
| 9,072,452 | B2 | 7/2015 | Vayser et al. |
| 9,072,455 | B2 | 7/2015 | Vayser et al. |
| D745,669 | S | 12/2015 | Swift |
| 9,198,566 | B2 | 12/2015 | Lia et al. |
| 9,229,165 | B2 | 1/2016 | Vayser et al. |
| 9,241,617 | B2 | 1/2016 | Grey et al. |
| D752,217 | S | 3/2016 | Swift |
| 9,271,709 | B2 | 3/2016 | Grey et al. |
| 9,271,710 | B2 | 3/2016 | Grey et al. |
| 9,282,878 | B2 | 3/2016 | Grey et al. |
| D753,295 | S | 4/2016 | Vivenzio et al. |
| 9,307,897 | B2 | 4/2016 | Swift |
| 9,308,054 | B2 | 4/2016 | Vayser et al. |
| 9,332,898 | B2 | 5/2016 | McMahon et al. |
| 9,429,746 | B2 | 8/2016 | Vayser et al. |
| 9,468,366 | B2 | 10/2016 | Grey et al. |
| 9,504,373 | B2 | 11/2016 | Vayser et al. |
| 9,510,737 | B2 | 12/2016 | Vayser et al. |
| 9,532,706 | B2 | 1/2017 | McMahon et al. |
| 9,574,742 | B2 | 2/2017 | Vayser et al. |
| 9,629,529 | B1 | 4/2017 | Indovina et al. |
| 9,636,004 | B2 | 5/2017 | Lia et al. |
| 9,636,182 | B2 | 5/2017 | Vayser et al. |
| 9,718,130 | B1 | 8/2017 | Vayser et al. |
| 9,763,743 | B2 | 9/2017 | Lin et al. |
| 9,808,231 | B2 | 11/2017 | Miraki et al. |
| 9,814,377 | B2 | 11/2017 | Lia et al. |
| 9,820,638 | B2 | 11/2017 | Cheng |
| 9,820,729 | B2 | 11/2017 | Miles et al. |
| 9,826,892 | B2 | 11/2017 | Dresher et al. |
| 9,833,295 | B2 | 12/2017 | Vayser et al. |
| 9,833,308 | B2 | 12/2017 | Dye |
| 9,844,364 | B2 | 12/2017 | Grey et al. |
| 9,861,349 | B2 | 1/2018 | Nadershahi et al. |
| 9,867,531 | B2 | 1/2018 | Pacey et al. |
| 9,867,602 | B2 | 1/2018 | Swift |
| 9,877,639 | B2 | 1/2018 | Grey et al. |
| 9,877,644 | B2 | 1/2018 | Greenstein et al. |
| D809,660 | S | 2/2018 | Nguyen et al. |
| 9,883,792 | B2 | 2/2018 | McMahon et al. |
| 9,888,957 | B2 | 2/2018 | Wolf et al. |
| 9,907,544 | B2 | 3/2018 | Nadershahi et al. |
| 9,913,682 | B2 | 3/2018 | Wolf et al. |
| 9,918,618 | B2 | 3/2018 | Molnar |
| 9,918,802 | B2 | 3/2018 | Coppersmith et al. |
| 9,931,028 | B2 | 4/2018 | Lia et al. |
| 9,943,295 | B2 | 4/2018 | King |
| 9,949,814 | B2 | 4/2018 | Alexander et al. |
| 9,955,858 | B2 | 5/2018 | Pamnani et al. |
| 9,968,262 | B2 | 5/2018 | Greenstein et al. |
| 9,968,346 | B2 | 5/2018 | Alexander et al. |
| 9,980,710 | B2 | 5/2018 | Seifert et al. |
| 9,986,901 | B2 | 6/2018 | Grey et al. |
| 9,986,903 | B2 | 6/2018 | Nadershahi et al. |
| 9,986,988 | B2 | 6/2018 | Ferro et al. |
| 9,999,345 | B2 | 6/2018 | Vayser et al. |
| 10,004,392 | B2 | 6/2018 | Millard et al. |
| 10,004,393 | B2 | 6/2018 | Kucklick |
| 10,028,648 | B2 | 7/2018 | Goldfain et al. |
| 10,028,649 | B2 | 7/2018 | Salvati et al. |
| 10,028,780 | B2 | 7/2018 | Wolf et al. |
| 10,045,686 | B2 | 8/2018 | Ou Yang et al. |
| 10,045,731 | B2 | 8/2018 | Prasad et al. |
| 10,052,432 | B2 | 8/2018 | Dexter et al. |
| 10,064,611 | B2 | 9/2018 | Ross et al. |
| 10,064,613 | B2 | 9/2018 | Davis et al. |
| 10,068,173 | B2 | 9/2018 | Vayser et al. |
| 10,092,176 | B2 | 10/2018 | Kienzle et al. |
| 10,092,281 | B2 | 10/2018 | Perler et al. |
| 10,098,530 | B2 | 10/2018 | McMahon et al. |
| 10,105,043 | B2 | 10/2018 | George |
| 10,117,646 | B2 * | 11/2018 | Friedrich ........... A61B 17/0293 |
| 10,130,441 | B2 | 11/2018 | Martinez |
| 10,166,016 | B2 | 1/2019 | Shimizu et al. |
| 10,172,601 | B2 | 1/2019 | Ahn |
| 10,174,933 | B2 | 1/2019 | Phillips, Jr. et al. |
| 10,188,298 | B2 | 1/2019 | Greenstein et al. |
| 10,213,271 | B2 | 2/2019 | Duggal et al. |
| 10,219,800 | B2 | 3/2019 | Tsubouchi |
| 10,220,445 | B2 | 3/2019 | Vayser et al. |
| 10,226,555 | B2 | 3/2019 | Vayser et al. |
| 10,238,462 | B2 | 3/2019 | Wood et al. |
| D846,119 | S | 4/2019 | Greeley et al. |
| 10,278,571 | B2 | 5/2019 | Poormand |
| 10,292,782 | B2 | 5/2019 | Haverich et al. |
| 10,292,784 | B2 | 5/2019 | Duggal et al. |
| 10,321,969 | B2 | 6/2019 | Wayne et al. |
| 10,342,525 | B2 | 7/2019 | Wilson |
| 10,456,190 | B2 | 10/2019 | Vayser et al. |
| 10,499,974 | B2 | 12/2019 | Heim et al. |
| 10,500,010 | B2 | 12/2019 | Vayser et al. |
| 10,512,518 | B2 | 12/2019 | Vayser et al. |
| 10,512,519 | B2 | 12/2019 | Swift et al. |
| 10,512,520 | B2 | 12/2019 | Wayne et al. |
| 10,531,933 | B2 | 1/2020 | Vayser et al. |
| 10,548,682 | B2 | 2/2020 | Vayser et al. |
| 10,568,712 | B2 | 2/2020 | Vayser et al. |
| 10,675,115 | B2 | 6/2020 | Vayser et al. |
| 10,729,511 | B2 | 8/2020 | Vayser et al. |
| 10,729,512 | B2 | 8/2020 | Wayne et al. |
| 10,966,702 | B1 * | 4/2021 | Swift ..................... A61B 17/02 |
| 11,540,817 | B2 | 1/2023 | Gallagher et al. |
| 11,622,758 | B2 | 4/2023 | Swift et al. |
| 11,744,568 | B2 | 9/2023 | Swift et al. |
| 2001/0029044 | A1 | 10/2001 | Gombrich et al. |
| 2002/0009275 | A1 | 1/2002 | Williams et al. |
| 2002/0022769 | A1 | 2/2002 | Smith et al. |
| 2002/0038075 | A1 | 3/2002 | Tsai |
| 2002/0038076 | A1 | 3/2002 | Sheehan et al. |
| 2002/0055670 | A1 | 5/2002 | Weiss |
| 2002/0115909 | A1 | 8/2002 | Bolser |
| 2002/0156350 | A1 | 10/2002 | Nieto |
| 2002/0165435 | A1 | 11/2002 | Weiss |
| 2002/0198471 | A1 | 12/2002 | Baxter-Jones et al. |
| 2003/0095781 | A1 | 5/2003 | Willaims |
| 2003/0105387 | A1 | 6/2003 | Frumovitz et al. |
| 2003/0139673 | A1 | 7/2003 | Vivenzio et al. |
| 2003/0158502 | A1 | 8/2003 | Baxter-Jones et al. |
| 2003/0176772 | A1 | 9/2003 | Yang |
| 2003/0187331 | A1 | 10/2003 | Faludi et al. |
| 2004/0026829 | A1 | 2/2004 | Van Der Weegen |
| 2004/0054260 | A1 | 3/2004 | Klaassen et al. |
| 2004/0141175 | A1 | 7/2004 | Baldwin et al. |
| 2004/0183482 | A1 | 9/2004 | Roberts et al. |
| 2004/0184288 | A1 | 9/2004 | Bettis |
| 2004/0186355 | A1 | 9/2004 | Strong |
| 2005/0033118 | A1 | 2/2005 | Berg |
| 2005/0065496 | A1 | 3/2005 | Simon et al. |

(56) References Cited

U.S. PATENT DOCUMENTS

2005/0085699 A1 4/2005 Weiss
2005/0085723 A1 4/2005 Huebner
2005/0093718 A1 5/2005 Martin
2005/0125015 A1 6/2005 McNally-Heintzelman et al.
2005/0159649 A1 7/2005 Patel
2005/0192482 A1 9/2005 Carpenter
2005/0215858 A1 9/2005 Vail, III
2005/0240081 A1 10/2005 Eliachar
2005/0277811 A1 12/2005 Richards et al.
2006/0084843 A1 4/2006 Sommerich et al.
2006/0122463 A1 6/2006 Klaassen
2006/0155276 A1 7/2006 Walulik et al.
2006/0189847 A1 8/2006 Yee et al.
2006/0200186 A1 9/2006 Marchek et al.
2007/0043264 A1 2/2007 Gillis et al.
2007/0060795 A1 3/2007 Vayser et al.
2007/0060938 A1 3/2007 Dziadik et al.
2007/0066872 A1 3/2007 Morrison et al.
2007/0100212 A1 5/2007 Pimenta et al.
2007/0158513 A1 7/2007 LeVahn et al.
2007/0208226 A1 9/2007 Grey et al.
2007/0230164 A1 10/2007 Vivenzio et al.
2007/0230167 A1 10/2007 McMahon et al.
2007/0255110 A1 11/2007 Wax et al.
2007/0270866 A1 11/2007 Von Jako
2007/0287888 A1 12/2007 Lovell et al.
2008/0002426 A1 1/2008 Vayser et al.
2008/0113312 A1 5/2008 Ortega
2008/0221569 A1 9/2008 Moore et al.
2008/0228038 A1 9/2008 McMahon et al.
2008/0269564 A1 10/2008 Gelnett
2008/0269565 A1 10/2008 Mcmahon et al.
2008/0278936 A1 11/2008 Kurth et al.
2009/0018400 A1 1/2009 Raymond et al.
2009/0069634 A1 3/2009 Larkin
2009/0097236 A1 4/2009 Miller et al.
2009/0112068 A1 4/2009 Grey et al.
2009/0275803 A1 11/2009 Krauter et al.
2009/0287192 A1 11/2009 Vivenzio et al.
2009/0312610 A1 12/2009 Buchok et al.
2010/0036382 A1 2/2010 Bonnadier
2010/0041955 A1 2/2010 Grey et al.
2010/0097794 A1 4/2010 Teng et al.
2010/0190129 A1 7/2010 Paz
2010/0191062 A1 7/2010 Kieffer
2010/0292533 A1 11/2010 Kasahara et al.
2011/0275894 A1 11/2011 Mackin
2012/0055470 A1 3/2012 Pecherer et al.
2012/0059226 A1 3/2012 Funt
2012/0078060 A1 3/2012 Swift
2012/0116170 A1 5/2012 Vayser et al.
2012/0232352 A1 9/2012 Lin et al.
2013/0018230 A1 1/2013 Su et al.
2013/0021798 A1 1/2013 Chen et al.
2013/0030254 A1 1/2013 Thalgott et al.
2013/0041229 A2 2/2013 Hahn et al.
2013/0092421 A1 4/2013 Kajiya
2013/0102850 A1 4/2013 Fiorella
2013/0102887 A1 4/2013 Thompson et al.
2013/0109910 A1 5/2013 Alexander et al.
2013/0158345 A1 6/2013 Majlessi
2013/0197313 A1 8/2013 Wan
2013/0245381 A1 9/2013 Dang et al.
2013/0245657 A1 9/2013 Deville et al.
2013/0267786 A1 10/2013 Vayser et al.
2013/0281784 A1 10/2013 Ray
2013/0324801 A1 12/2013 Grey et al.
2014/0088371 A1 3/2014 Vayser et al.
2014/0179998 A1 6/2014 Pacey et al.
2014/0202459 A1 7/2014 Iqbal
2014/0228875 A1 8/2014 Saadat
2014/0257039 A1 9/2014 Feldman
2014/0275790 A1 9/2014 Vivenzio et al.
2014/0309499 A1 10/2014 Swift
2014/0316211 A1 10/2014 Hermle
2014/0323800 A1 10/2014 Dye
2014/0364695 A1 12/2014 Nadershahi et al.
2014/0371536 A1 12/2014 Miller et al.
2015/0018625 A1 1/2015 Miraki et al.
2015/0157469 A1 6/2015 Prado et al.
2015/0238070 A1 8/2015 Lia et al.
2015/0285382 A1 10/2015 Kienreich et al.
2016/0000305 A1 1/2016 Elbaz et al.
2016/0030128 A1 2/2016 Duggal et al.
2016/0038032 A1 2/2016 Dan
2016/0066915 A1 3/2016 Baber et al.
2016/0081833 A1 3/2016 Leblanc et al.
2016/0095506 A1 4/2016 Dan et al.
2016/0100751 A1 4/2016 Davis et al.
2016/0151058 A1 6/2016 Ferro et al.
2016/0302657 A1 10/2016 Hussey et al.
2017/0007228 A1 1/2017 Costabile
2017/0020621 A1 1/2017 Huldin et al.
2017/0059400 A1 3/2017 Murphy et al.
2017/0065282 A1 3/2017 Mathis et al.
2017/0079518 A1 3/2017 Elbaz et al.
2017/0172404 A1 6/2017 McMahon et al.
2017/0172555 A1 6/2017 Shimizu et al.
2017/0181605 A1 6/2017 Lalli et al.
2017/0181607 A1 6/2017 Lalli et al.
2017/0181615 A1 6/2017 Vella et al.
2017/0181616 A1 6/2017 Vella et al.
2017/0224206 A1 8/2017 Vayser
2017/0231712 A1 8/2017 Vayser
2017/0296162 A1 10/2017 Wan
2017/0300623 A1 10/2017 Rosenblatt et al.
2017/0303903 A1 10/2017 De Koning et al.
2017/0347871 A1 12/2017 Wallace et al.
2017/0360423 A1 12/2017 Stevenson et al.
2018/0000469 A1 1/2018 Wood et al.
2018/0008137 A1 1/2018 Poormand
2018/0008138 A1 1/2018 Thommen et al.
2018/0008368 A1 1/2018 Duggal et al.
2018/0014721 A1 1/2018 Rullo et al.
2018/0014842 A1 1/2018 Shener-Irmakoglu
2018/0014900 A1 1/2018 Vayser et al.
2018/0036095 A1 2/2018 Vayser et al.
2018/0042596 A1 2/2018 Tsubouchi
2018/0064316 A1 3/2018 Charles et al.
2018/0064317 A1 3/2018 Tesar
2018/0078301 A1 3/2018 Vayser
2018/0110505 A1 4/2018 Farley
2018/0116581 A1 5/2018 Prasad et al.
2018/0125336 A1 5/2018 Goldfarb et al.
2018/0125347 A1 5/2018 Czyzewski et al.
2018/0132710 A1 5/2018 Pacey et al.
2018/0132970 A1 5/2018 Ritter
2018/0153391 A1 6/2018 McMahon et al.
2018/0156448 A1 6/2018 Phillips, Jr. et al.
2018/0206832 A1 7/2018 Greeley et al.
2018/0228376 A1 8/2018 Greenstein et al.
2018/0228483 A1 8/2018 Duggal et al.
2018/0235444 A1 8/2018 Tsai
2018/0235592 A1 8/2018 Kass et al.
2018/0249902 A1 9/2018 Grey et al.
2018/0263480 A1 9/2018 Lalli et al.
2018/0271581 A1 9/2018 Ou Yang et al.
2018/0280011 A1 10/2018 Ferro et al.
2018/0296082 A1 10/2018 Salvati et al.
2018/0296204 A1* 10/2018 Davis .................. A61B 1/0615
2018/0317746 A1 11/2018 Lalli et al.
2018/0317752 A1 11/2018 Cybulski et al.
2018/0317902 A1 11/2018 Green et al.
2018/0328572 A1 11/2018 Kennedy et al.
2019/0038273 A1 2/2019 Perler et al.
2019/0049655 A1 2/2019 Zagatsky et al.
2019/0076138 A1 3/2019 Opperman
2019/0083079 A1 3/2019 Shimizu et al.
2019/0133432 A1 5/2019 Tsai
2019/0143006 A1 5/2019 Vayser et al.
2019/0143414 A1 5/2019 Vayser et al.
2019/0150422 A1 5/2019 Welch
2019/0150725 A1 5/2019 Ramanujam et al.
2019/0150739 A1 5/2019 Wawro et al.

(56) References Cited

U.S. PATENT DOCUMENTS

| | | | |
|---|---|---|---|
| 2019/0150786 A1 | 5/2019 | Vassallo et al. | |
| 2019/0167111 A1 | 6/2019 | Greenstein et al. | |
| 2019/0167378 A1 | 6/2019 | Wood et al. | |
| 2019/0190293 A1 | 6/2019 | Wawro et al. | |
| 2019/0223708 A1 | 7/2019 | Recanati et al. | |
| 2019/0254512 A1 | 8/2019 | Spiertz | |
| 2019/0254771 A1* | 8/2019 | Swift | A61B 1/00032 |
| 2019/0335988 A1 | 11/2019 | Lia et al. | |
| 2019/0343379 A1 | 11/2019 | Altamura | |
| 2019/0365217 A1 | 12/2019 | Hegenberger | |
| 2020/0008694 A1 | 1/2020 | Karla et al. | |
| 2020/0046216 A1 | 2/2020 | Moein | |
| 2020/0069171 A1 | 3/2020 | Miller et al. | |
| 2020/0107714 A1 | 4/2020 | Bar-Or et al. | |
| 2020/0253467 A1 | 8/2020 | Lees, Jr. et al. | |
| 2020/0337541 A1 | 10/2020 | Vivenzio et al. | |
| 2021/0145270 A1 | 5/2021 | Altamura | |

FOREIGN PATENT DOCUMENTS

| | | | |
|---|---|---|---|
| CN | 2516109 | Y | 10/2002 |
| CN | 2629738 | Y | 8/2004 |
| CN | 1565664 | A | 1/2005 |
| CN | 2668152 | Y | 1/2005 |
| CN | 1717195 | A | 1/2006 |
| CN | 101179982 | A | 5/2008 |
| CN | 201055387 | Y | 5/2008 |
| CN | 203591245 | U | 5/2008 |
| CN | 201139589 | Y | 10/2008 |
| CN | 102415869 | A | 4/2012 |
| CN | 103154793 | A | 6/2013 |
| CN | 302536685 | S | 8/2013 |
| CN | 103925266 | A | 7/2014 |
| CN | 203898367 | U | 10/2014 |
| CN | 102573700 | B | 12/2014 |
| DE | 2128855 | A | 12/1972 |
| DE | 10216618 | A1 | 1/2003 |
| DE | 202004002963 | U1 | 5/2004 |
| DE | 102005002220 | A1 | 10/2005 |
| DE | 202005019780 | U1 | 5/2006 |
| DE | 600 33 612 | T2 | 12/2007 |
| DE | 202010017638 | U | 5/2012 |
| EP | 0190014 | A2 | 8/1986 |
| EP | 1074224 | A2 | 7/2001 |
| FR | 2490478 | A1 | 3/1982 |
| GB | 2505463 | A | 5/2014 |
| RU | 2187972 | C2 | 8/2002 |
| RU | 2308873 | C2 | 10/2007 |
| WO | 9825512 | A1 | 6/1998 |
| WO | WO 2000054663 | A1 | 9/2000 |
| WO | 0137739 | A1 | 5/2001 |
| WO | 01/62137 | A2 | 8/2001 |
| WO | 03082123 | A2 | 10/2003 |
| WO | 2004064624 | A1 | 8/2004 |
| WO | 2006107877 | A2 | 10/2006 |
| WO | 2006107878 | A2 | 10/2006 |
| WO | 2007/084641 | A2 | 7/2007 |
| WO | 2009/090383 | A2 | 7/2009 |
| WO | 2009137017 | A2 | 11/2009 |
| WO | 2013-044151 | A1 | 3/2013 |
| WO | 2014-041172 | A1 | 3/2014 |
| WO | 2006121530 | A2 | 11/2016 |
| WO | 2016196788 | A1 | 12/2016 |

OTHER PUBLICATIONS

International Search Report, for International application No. PCT/US2016/035508 issued Sep. 15, 2016 for corresponding U.S. application, U.S. Appl. No. 15/171,581.
International Search Report for International application No. PCT/US2016/036833 issued Jan. 19, 2017.
An Office Action issued in U.S. Appl. No. 15/171,581.
A PCT Search Report issued in PCT Application No. PCT/US2017/042617.
A Nov. 1, 2017 Chinese Office Action, without an English Translation, that issued in Chinese Patent Application No. 201510543086.7.
The Jul. 16, 2018 Chinese Office Action, without an English Translation, that issued in Chinese Patent Application No. 201510543086.7.
Solvey, Techinical Data Sheet, Ixef 1022 polyarylamide, Feb. 13, 2015, pp. 1-5.
http://www.makeitfrom.com/material-properties/Polyetheretheketone-PEEK, printed on Oct. 9, 2016, pp. 1-9.
International Search Report for International application No. PCT/US2021/017768 issued May 27, 2021.
International Search Report for International application No. PCT/US2021/014076 issued Apr. 15, 2021.
https://web.archive.org/web/20160618175418/http://bihlermed.com:80/scintillant/; Home—Scintillant® Surgical Light : Scintillant® Surgical Light; printed Oct. 19, 2022 (One Page).
A European Search Report issued on Nov. 23, 2018, that issued in the corresponding European Patent Application No. 16747107.7.
A Oct. 29, 2018 Chinese Office Action, without an English Translation, that issued in Chinese Patent Application No. 201711159829.6.
International Search Report of PCT/US2018/054925, Oct. 9, 2018.
Pankaj Saxena, et al., Hydrodissection Technique of Harvesting Left Internal Thoracic Artery, Department of Cardiac Surgery, The Prince Charles Hospital, Chermside, Brisbane, Queensland, Australia, Thoracic Artery, Ann Thorac Surg., 2005; 80:335-6.
A Supplementary European Search Report issued on Apr. 24, 2019, that issued in European Patent Application No. 16804432.9.
OBP Medical—OfficeSPEC, Premier Speculum for In-Office Procedures published Nov. 30, 2009 (1 page).
OBP Medical—ER-Spec OBGYN Brochure published Nov. 19, 2014 (2 pages).
OBP Medical—ER-Spec Brochure, Light Source Now 10X Brighter published Oct. 30, 2012 (1 page).
OBP Medical—ER-Spec Product Presentation published Apr. 16, 2014 (12 pages).
OBP Medical—ER-Spec Brochure published Apr. 11, 2013 (2 pages).
OBP Medical—ER-Spec Brochure published Feb. 4, 2013 (2 pages).
OBP Medical—ER-Spec Brochure, Light Source Now 10X Brighter published Jan. 23, 2013 (1 page).
Redefining illumination, Eikon LT Adapt SE For optimal precision and protection (2019), Stryker, www.stryker.com/surgical (3 pages).
International Search Report and Written Opinion in International Appln. No. PCT/US2024/038500, mailed on Jan. 16, 2025, 12 pages.

* cited by examiner

ILLUMINATED SURGICAL RETRACTOR CAPABLE OF HAND-HELD OPERATION AND OF BEING MOUNTED TO A FIXED FRAME

FIELD OF INVENTION

The present invention relates to surgical devices and, more particularly, to illuminated surgical retractors capable of being selectively used as hand-held retractors and mounted to a fixed frame or fixed arm of a surgical positioning device and further being suitable for use for soft tissue retraction and for spinal surgical procedures.

BACKGROUND

Illuminating body cavities using a medical device is a well-documented problem in the medical field. In one aspect, existing medical devices fail to provide sufficient illumination. That is, most medical devices with integrated light sources often fail to direct or concentrate illumination to a desired surgical field. In other cases, existing medical devices illuminate an overly large area and create a glare that interferes with a physician's field of view. In another aspect, current lighting technology creates heat as a by-product. U.S. Pat. No. 10,512,519, assigned to the same assignee herein and incorporated herein by reference, discloses improved surgical devices, including surgical retractors, which address these problems in retractors and other medical devices.

A new trend in illuminated medical and surgical devices is a "single-use" configuration that eliminates a need for sterilization or a risk of cross contamination. Such medical devices are generally manufactured with light and inexpensive materials, such as plastic, and are wholly disposable after a single use. However, during many surgical procedures, multiple "single-use" and non-disposable devices are used during surgical procedures. As a result, selection and subsequent disposal of devices necessary for a particular procedure is often a complicated process, increasing complexity and costs.

SUMMARY OF THE INVENTION

The present invention provides a surgical device, and specifically, surgical retractor that can be utilized during spinal surgical procedures as well as in other surgical procedures. In addition, the present invention provides a surgical retractor which can interchangeably be used independently as a hand-held surgical retractor and as a fixed retractor mounted to a fixed frame or a fixed arm of a surgical positioning device or other mounting system, without substantially changing the configuration of the surgical retractor.

In accordance with the present invention a surgical retractor includes a handle, and a blade extending from the handle, and the handle has an ergonomic construction configured for hand-held use of the retractor, wherein the handle is further configured to attach to one or more of a fixed frame and a fixed arm of a surgical positioning device. In some embodiments, the handle has a hollow construction.

In certain embodiments, the retractor further includes an illumination assembly including at least one direct light source provided on the blade, and one or more electrical components housed in the handle. The illumination assembly may include one or more power sources housed in the handle. In certain embodiments, the handle is configured to attach to one or more of the fixed frame and the fixed arm via a mounting adapter provided on the handle. The handle may be configured to releasably engage with the mounting adapter for attaching to one or more of the fixed frame and the fixed arm. In some embodiments, the handle includes a main portion extending from the blade and a curved distal end portion offset from a longitudinal axis of the main portion, wherein the mounting adapter is provided on the curved distal end portion. In particular, the blade extends from the handle in a first direction and the curved distal end portion curves toward a second direction opposite of the first direction. The handle includes a first surface, at least a portion of the first surface facing in the first direction, and a second opposing surface, and in some embodiments, the mounting adapter is provided on the first surface of the curved distal end portion. In some embodiments, the curved distal end portion is configured to releasably engage with the mounting adapter, wherein the curved distal end portion includes a recess configured to receive a portion of the mounting adapter so as to engage with the mounting adapter. In some embodiments, the retractor further includes the mounting adapter including a connector tip configured to attach to a corresponding connector of one or more of the fixed frame and the fixed arm and a coupling extension configured to engage with the recess in the curved distal end portion of the handle. A shape of the coupling extension may correspond to a shape of the recess in the curved distal end portion of the handle. In some embodiments, the mounting adapter further includes a fastener for securing the engagement between the coupling extension and the recess in the curved distal end portion when the coupling extension is inserted into the recess.

Further in accordance with the present invention, a surgical retractor comprises: a main body forming a handle and a blade extending from the handle, the main body forming one or more cavities therein and having an open side, a blade cover configured to attach to the main body and to cover at least a portion of the open side of the main body along the blade, wherein the blade cover includes a least one channel providing an enclosed passage between a first opening adjacent a proximal end portion of the blade and a second opening adjacent a distal end portion of the blade. The at least one channel is configured to allow insertion of one or more instruments therethrough. In some embodiments, the at least one channel is partially embedded into a thickness of the blade. The at least one channel may extend along a majority of a length of the blade.

In certain embodiments, the blade cover includes first and second sides and first and second channels, and the first channel extends adjacent the first side of the blade cover while the second channel extends adjacent the second side of the blade cover. In some embodiments, the retractor further comprises an illumination assembly, at least a portion of the illumination assembly being housed within the one or more cavities in the main body. The illumination assembly includes one or more direct light sources positioned on the blade cover, with the blade cover including first and second channels, wherein the one or more direct light sources are provided between the first and second channels. In some embodiments, the retractor further includes a smoke evacuation adapter configured to releasably connect to at least one of the first and second channels and to fluidly connect the at least one of the first and second channels to a suction port in the handle.

In certain embodiments, the blade includes an atraumatic curved tip extending from the distal end portion of the blade for providing soft tissue retraction and vein retraction. In some embodiments, the blade cover forms a bottom surface of the blade and the main body forms the opposing top surface of the blade, and the atraumatic curved tip extends from the top surface of the blade. A width the atraumatic curved tip may taper toward a distal tip of the blade. In some embodiments, a proximal end of the atraumatic curved tip attached to the distal end portion of the blade has a smaller width than the rest of the distal end portion.

BRIEF DESCRIPTION OF THE DRAWINGS

The above and other features and aspects of the present invention will become more apparent upon reading the following detailed description in conjunction with the accompanying drawings, in which.

DETAILED DESCRIPTION

Figure 1A:
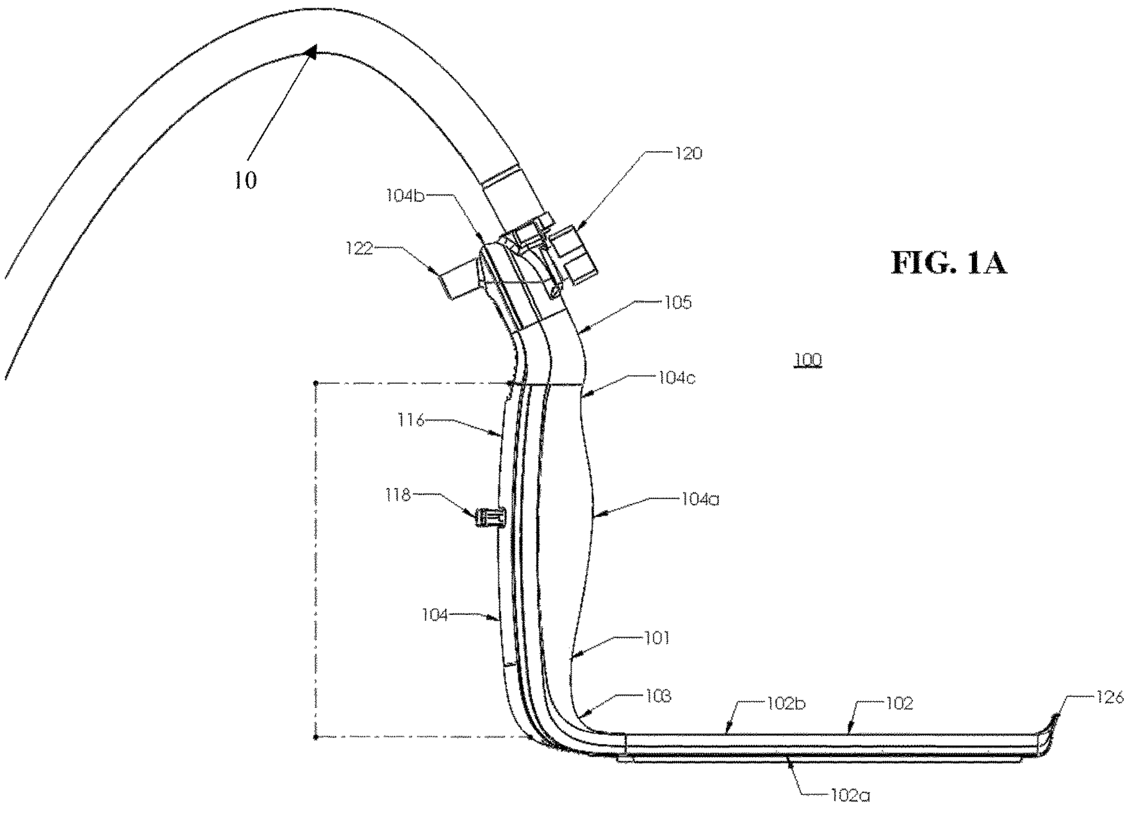
FIGS. 1A-1E show a surgical retractor in accordance with the present invention from different angles of view.

The present invention is an improved surgical retractor that includes some or all of the features of the surgical retractor described in U.S. Pat. No. 10,512,519, assigned to the same assignee herein and incorporated herein by reference. The improved surgical retractor of the present invention is configured to be used independently as a hand-held retractor and as a fixed-frame retractor configured to be affixed to a frame or a fixed arm of a surgical positioning device, such as a mounted surgical holding system or another surgical holder and positioning arm system. Specifically, when needed, the improved surgical retractor of the present invention can be held and operated by a user performing a surgical procedure, i.e., hand-held operation, and is also configured to easily attach to a Quick-connect fitting of a fixed frame or fixed arm of a surgical positioning device/stationary positioning system, including systems and devices compatible with laparoscopic procedures, spine and orthopedic procedures, robotic procedures, etc.

Moreover, the improved surgical retractor of the present invention has improved features discussed in more detail below that allow the retractor to be used for spine and orthopedic surgical procedures as well as for soft-tissue surgical procedures. The improved surgical retractor includes enclosed channels on the blade which can be used for insertion of instruments and equipment, and may be adapted for smoke evacuation with an appropriate adapter. The improved surgical retractor also includes an atraumatic curved tip that can be used for soft tissue retraction, for cradling a vein and for vein retraction. These features are discussed in more detail below with reference to the accompanying figures.

FIGS. 1A-1E show overall assembled views of the retractor 100 of the present invention. The retractor 100 includes a main body 101 forming a blade 102 and a handle 104. The blade 102 has a first (bottom) surface **102*a* and an opposing second (top) surface 102*b* and a proximal end and a distal end. The proximal end is defined herein as the end of the blade 102 closer to the handle 104 of the retractor 100 and the distal end is defined as the tip end of the blade opposite the proximal end. The handle 104 extends from the blade 102 at an angle, with a curved joint or a saddle portion 103 joining the handle 104 to the blade 102**.

The main body 101 of the retractor 100 may be formed as an integral frame forming the blade 102 and the handle 104 and forming one or more cavities therein for housing internal components, including electrical components, of the retractor 100. One or more covers are used for covering the cavities formed in the frame of the main body 101 as discussed in more detail below with respect to FIG. 2. In some embodiments, portions of the frame may be separately formed and assembled together to form the frame. In the assembled retractor, the handle 104 has a hollow interior which houses a plurality of components therein, and the blade is configured to accommodate a pair of enclosed channels passing therethrough and at least a portion of an illumination assembly for providing illumination from the blade to a target site, such as a surgical incision.

The retractor 100 of the present invention includes the illumination assembly with one or more direct light sources 112 provided on the blade 102. The one or more direct light sources 112 suitable for use in the illumination assembly include, but are not limited to, light-emitting diodes (LEDs), Organic LEDs (OLED), polymer LEDs (PLEDs), laser lights, incandescent lights, CFL, halogen lights, etc. In some embodiments, different types of light sources are used in the same device, and in some embodiments, brightness of the light sources within the same retractor is varied so as to accomplish desired illumination.

In the illustrative embodiment of FIGS. 1A-1E, the illumination assembly includes at least one direct light source **112*a* positioned so as to emit light in a direction of the distal end of the blade and one or more direct light sources 112*b* positioned at one or more different angles on a surface of the blade. In FIGS. 1A-1E, the one or more direct light sources 112*b* are positioned on the bottom surface 102*a* of the blade 102. The angles of the one or more direct light sources are chosen so that light projections resulting from the light sources illuminate both the area near the distal end of the blade 102 and the area above the surface of the retractor blade 102**. In some embodiments, the angles of the direct light sources may be adjustable.

Figure 1B:
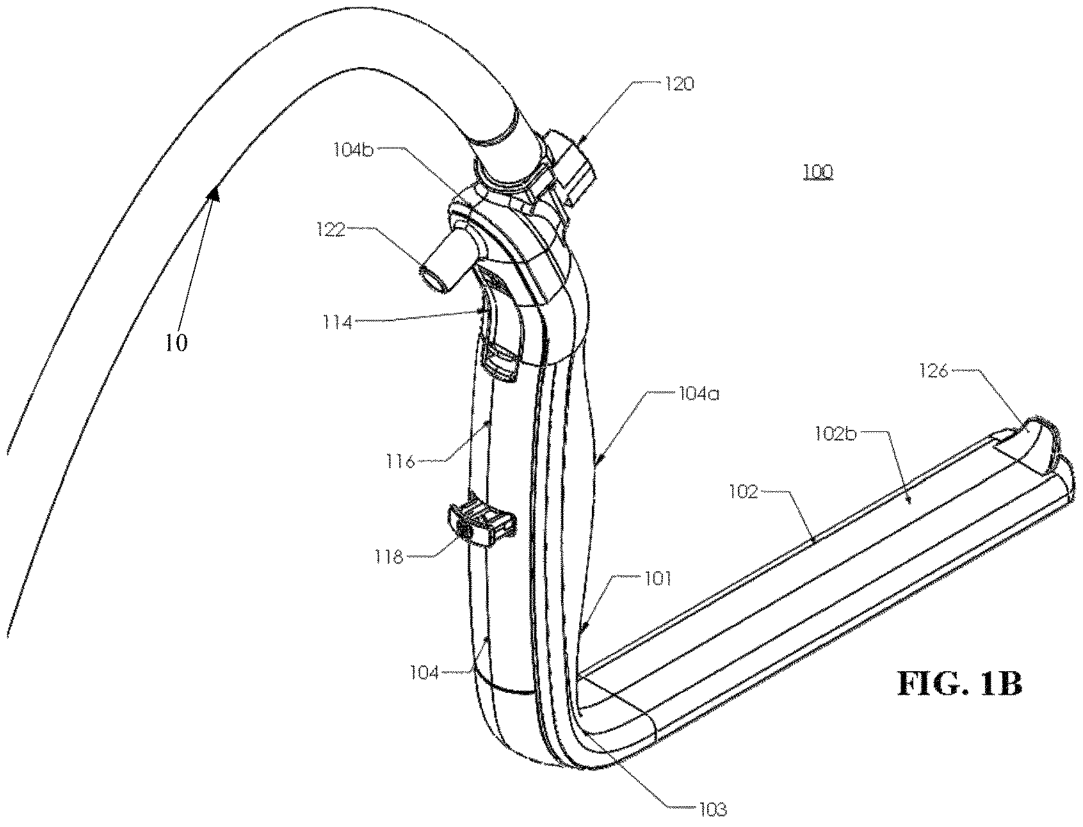
Figure 1C:
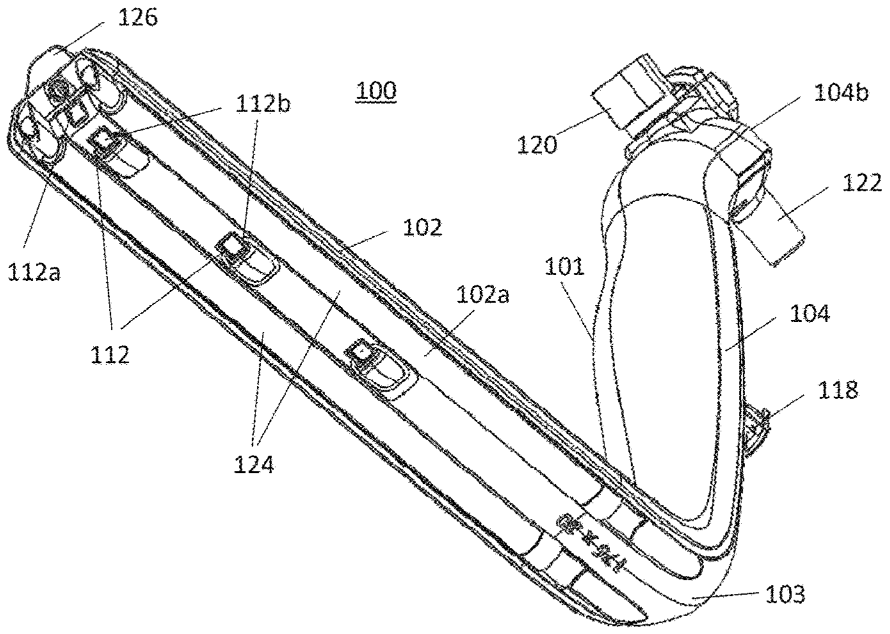
Figure 1D:
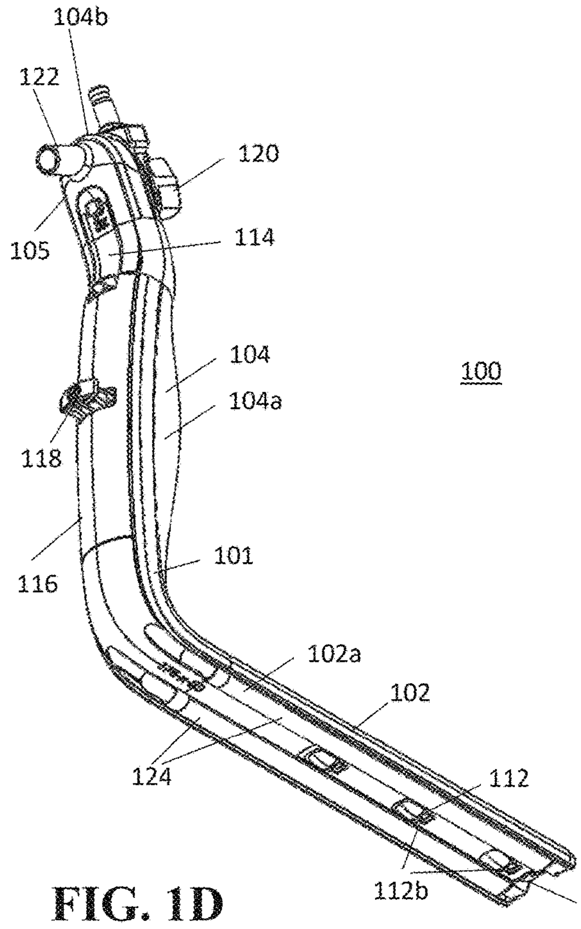
Figure 1E:
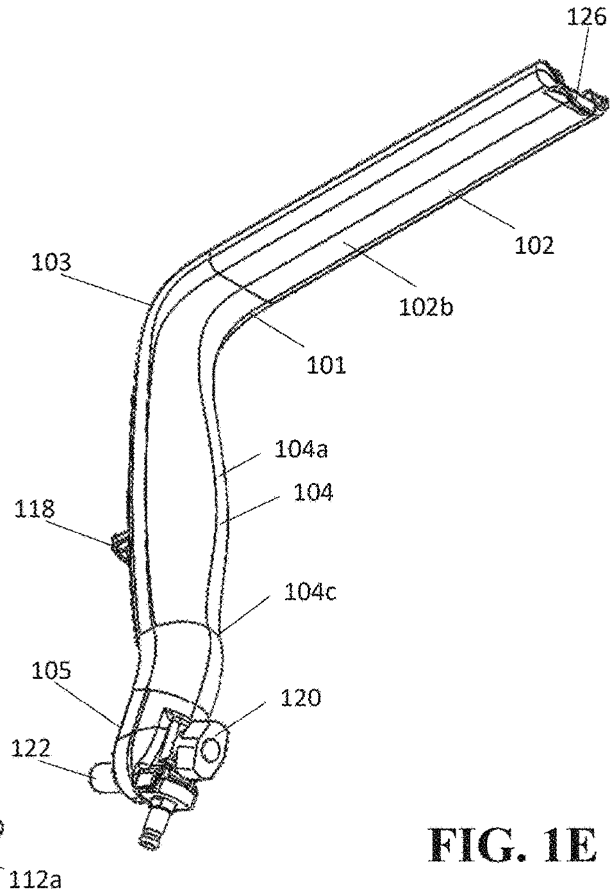
Figure 2:
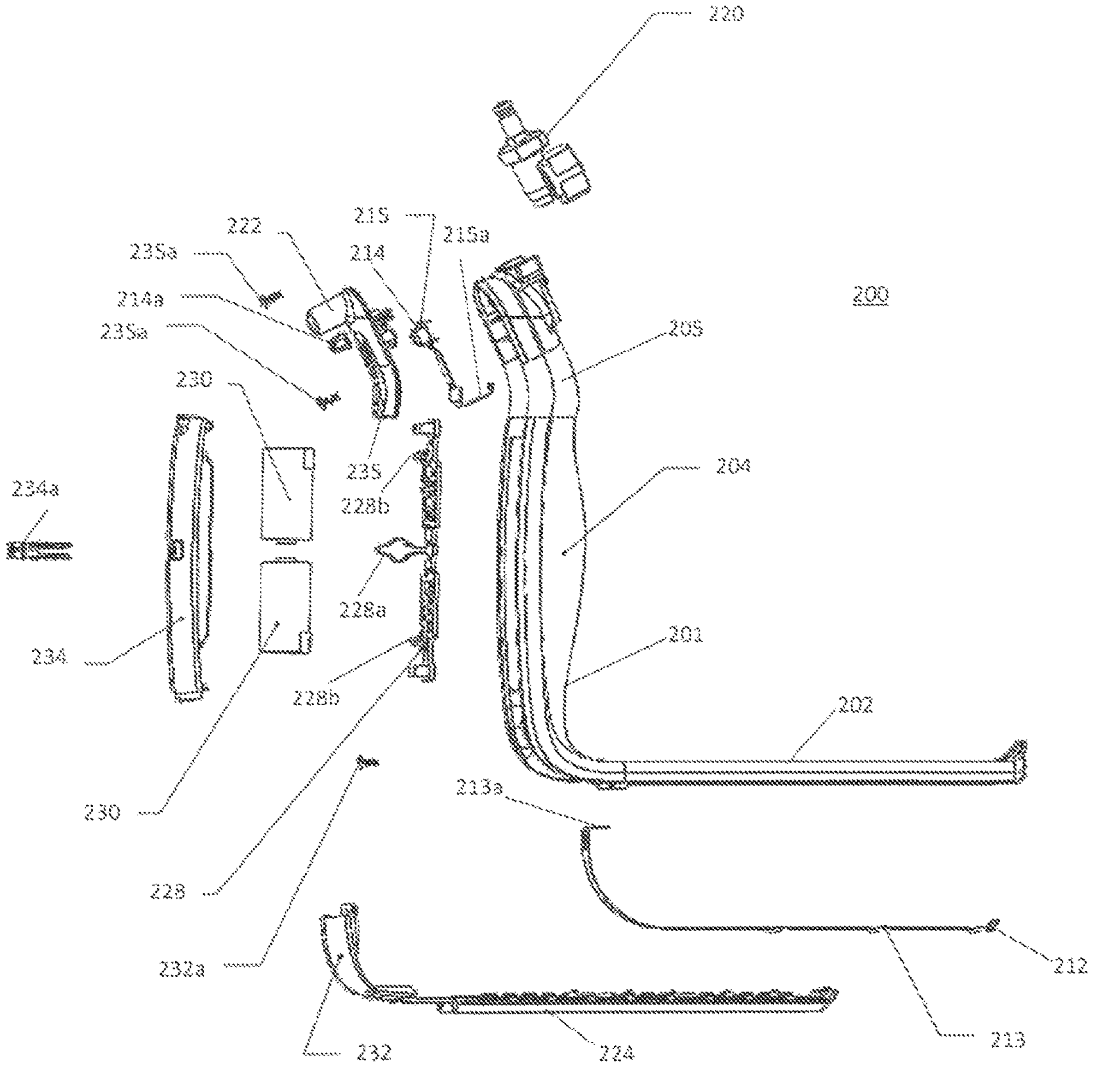
FIG. 2 shows an exploded view of the surgical retractor of FIGS. 1A-1E.

As discussed in more detail with respect to FIG. 2, the illumination assembly also includes a power source, such as one or more batteries, and an operating assembly 114 with operation member for activating the one or more direct light sources 112 and controlling illumination provided by the one or more direct light sources. The operating assembly 114 may include a button, a switch, a potentiometer, a slide switch, any combination thereof, or any other suitable device for controlling the turning ON/OFF of the one or more direct light sources. The operating assembly 114 may also control the brightness, color and/or direction of the light being emitted from the one or more direct light sources. In one illustrative embodiment, the power source is housed within the handle 104 and the operating assembly 114 is provided near the distal end of the handle 104. As can be seen from FIGS. 1A-1E, a battery cover 116 with a push-tab assembly 118, similar to the one described in U.S. Pat. No. 10,512,519 and incorporated herein by reference, covers the battery compartment in the handle 104 and has a function of assisting in battery removal to prevent contamination of the batteries during the removal process.

In the embodiment of FIGS. 1A-1E, the handle 104 of the retractor is ergonomic and is specifically configured to provide comfort to the user while using the retractor as a hand-held retractor. This requires the handle 104 to have sufficient length to accommodate a user's hand so that the user can comfortably hold the handle 104 of the retractor when used as a hand-held retractor. In addition, the curvature of the handle 104 in FIGS. 1A-1E allows the retractor to be attached to a fixed frame or a fixed arm of a surgical holding system.

As shown in FIGS. 1A-1E, the handle 104 extends from the curved joint 103 to a distal end 104*b* and has a front surface that faces in the same direction as the blade extension and an opposing rear surface. In the illustrative configuration of FIGS. 1A-1E, the front surface of the handle 104, as well as the sides thereof are formed by the main body 101 of the retractor, while the rear surface is formed by the cover(s) covering the main body 101. The front surface of the handle 104 includes a curved protrusion 104*a* or convexity extending around its central area, about mid-length of the handle 104. In the illustrative example of FIGS. 1A-1E, the curved protrusion 104*a* is part of the frame forming the main body 101 of the retractor. This curved protrusion 104*a* provides a comfortable and ergonomic grip for the operator when holding the retractor and using the retractor as a hand-held retractor in different orientations, and also provides additional space for accommodating the batteries and other components within the cavity of the handle 104.

The distal end 104*b* of the handle 104 extends into curved end portion 105 which is offset from the plane along the length of the handle 104. In the embodiment shown in FIGS. 1A-1E, the curved end portion 105 curves in a direction substantially opposite from the direction of the blade extension and in a direction away from the curved protrusion 104*a*. The curved end portion 105 may be angled 60-180° with reference to the top surface 102*b* of the blade 102. In the illustrative embodiment of FIGS. 1A-1E, the curved end portion 105 is angled about 100-130° with reference from the top surface 102*b* of the blade 102, and in the specific example of FIGS. 1A-1E, about 115° with reference to the top surface 102*b* of the blade 102. The curved end portion 105 allows for a mounting adapter 120 to be connected thereto for connecting the retractor to a fixed frame or fixed arm 10 of a surgical positioning device. The curvature of the curved end portion 105 also allows the retractor 100 to be positioned, when attached to a surgical positioning device, so as to not interfere with a patient or nearby equipment. In addition, the curvature of the curved end portion 105 avoids interference of the mounting adapter with hand-held operation of the retractor 100.

In the illustrative embodiment of FIGS. 1A-1E, an indentation or a concavity 104*c* may be formed in the front surface of the handle between the curved protrusion 104*a* of the handle and the curved end portion 105. The concavity 104*c* further improves the ergonomic characteristics of the handle 104 and functions to keep the operator's hand from accidentally slipping down to the curved end portion 105.

As mentioned herein above, in order to provide sufficient comfort to a user while holding the retractor, the handle is required to have sufficient length to accommodate the user's whole hand. In the illustrative embodiment shown in FIG. 1A, a length L of the handle from the top surface of the blade to the end of the concavity 104*c* is at least 3 inches, and in some embodiments, at least 5 inches. In some embodiments, the length L is at least 3.5 inches, or at least 4 inches or at least 4.5 inches or at least 5 inches. In certain embodiments, the length L is selected between 3 and 10 inches, and in some embodiments, between 3 and 7 inches, or between 4 and 6 inches. In one illustrative example, the length L is 132.2 mm or 5.2 inches.

In the retractor of the present invention, the operating assembly 114 and a connection for the mounting adapter 120 are provided on opposing sides of the curved end portion 105. As shown in FIGS. 1A-1E, the operating assembly 114 is provided on the rear surface of the handle on the curved end portion 105. In this exemplary embodiment, the operating assembly 114 is incorporated within a concave curvature of the rear surface of the curved end portion 105. This positioning of the operating assembly allows for one hand operation and control of the retractor and of the illumination assembly of the retractor. With this configuration, an operator can hold the retractor in either hand and in any orientation and can operate the operating assembly 114 on the curved end portion 105 with a thumb or a pinky finger without requiring overextending of the user's hand.

In FIGS. 1A-1E, the curved end portion 105 includes the connection for attaching the mounting adapter 120 on the front surface thereof to provide for attaching the retractor 100 to a fixed arm 10 or fixed frame of a surgical holding system. In some embodiments, the mounting adapter 120 is removable from the curved end portion 105, while in other embodiments, the mounting adapter 120 may be permanently affixed to, or integrally formed with, the curved end portion. An exemplary configuration of the curved end portion 105 and of the mounting adapter 120 attached thereto will be described with reference to FIGS. 3A-3I.

In addition, the curved end portion 105 includes a suction port 122 for connecting to a vacuum source to provide smoke evacuation through the handle 104 of the retractor. The suction port 122 is provided on the rear surface of the curved portion at or near the distal end 104*b* of the handle so as to avoid any interference with a user's hand-held operation of the retractor. As can be seen in FIGS. 1C and 1D and as described in more detail below with respect to FIG. 5, the blade 102 includes one or more through channels 124 extending along at least a portion of the length of the blade and having multiple functions depending on the use of the retractor. A smoke evacuation adapter may be attached to the retractor to allow for smoke evacuation through the channels 124 and through the handle 104 when the suction port 122 is connected to a vacuum source.

As shown in FIGS. 1A-C and 1E and also described in more detail below with respect to FIGS. 4A-4C, the distal end of the blade 102 includes an atraumatic curved tip 126. The curved tip 126 can be used for soft tissue retraction as well as for vein retraction and may also be used for cradling a vein.

FIG. 2 shows an exploded view of the retractor 200, which can be the retractor of FIGS. 1A-1E, and its internal components. As shown, the retractor 200 includes a main body 201 forming the blade 202 and the handle 204 with the curved end portion 205. In the present illustrative embodiment, the blade and handle portions of the main body 201 are integrally formed as a single piece. However, in other embodiments, the blade and handle portions may be separately formed and coupled to one another. The handle 204 has a hollow interior which is configured to accommodate at least some of the electrical components of the illumination assembly. The blade 202 is also configured to accommodate one or more direct light sources 212 and connections between the light sources and the remaining components of the illumination assembly.

As shown in FIG. 2, the retractor 200 also includes a blade cover 232 configured to attach to and cover the blade portion of the main body 201, a battery cover 234 configured to attach to and cover most of the handle portion of the main body 201 and a curved end portion cover 235 configured to attach to and cover the curved end portion 205 of the main body 201. The blade cover 232 includes one or more openings (visible in FIGS. 1C and 1D) for positioning and/or exposing one or more light sources (e.g., LEDs) and corresponding in positions to the positions of the one or more light sources on the blade. The blade cover 232 also includes or more channels 224 formed on its outer surface and extending along at least a portion of the length of the blade. As can be seen in FIGS. 1C and 2D, two channels 124/224 are formed on the blade cover, each extending along a side of the blade cover with the light sources 112/212 being positioned centrally between the two channels 124/224. A more detailed description of the channels 224 is provided below with respect to FIG. 5.

In the configuration of the retractor of FIG. 2, the light sources are provided on, and are electrically connected via, an LED flex circuit 213 that functions as and/or replaces separate LEDs and wiring connecting the LEDs in conventional lighting assemblies. The LED flex circuit 213 includes a flexible substrate, such as a flexible strip, with one or more LEDs 212 mounted thereon, and incorporates wiring and electrical connections in the flexible substrate for electrically connecting the LED(s) to the power source and to the operating assembly 214. The flexible substrate may also incorporate therein one or more circuits for controlling the operation of the LEDs. The LED flex circuit 213 includes a connecting portion 213*a* that connects to other electrical components, e.g., the PCB described below, of the illumination assembly. The LED flex circuit 213 may include heat dissipating features, such as one or more copper layers on the flexible substrate as described in U.S. Pat. No. 10,512,519 incorporated by reference herein.

The LED flex circuit 213 is positioned between the blade portion of the main body 201 and the blade cover 232, which in the embodiment of FIG. 2 covers the entire length or substantially the entire length of the LED flex circuit 213. A distal end of the blade cover 224 covers the corresponding end of the LED flex circuit 213 and includes an opening for an LED mounted at the end of the LED flex circuit 213. A proximal end of the blade cover 232 may end at the proximal end of the blade or as shown in FIG. 2, may extend to cover the curved joint that connects the blade to the handle and in some cases, may extend to cover a proximal end portion of the handle. The blade portion of the main body and/or the blade cover 232 may include internal projections thereon to retain and position the LED flex circuit 213 and the LEDs mounted thereon relative to the blade portion and the blade cover 232.

The blade cover 232 may be press fit or snap fit with the blade portion of the main body 201. U.S. Pat. No. 10,512,519, incorporated herein by reference, discloses an exemplary construction of the blade cover and the blade portion that allows the blade cover to be press-fit with the blade portion. In one embodiment, one of the blade cover and the blade portion of the main body includes a plurality of pins or posts while the other of the blade cover and blade portion of the main body includes a plurality of openings in corresponding positions so that the plurality of pins or posts can be press-fit into the plurality of corresponding openings. In other embodiments, the blade cover and the blade portion of the main body include projections and corresponding recesses that allow the blade cover to snap fit to attach to the blade portion of the main body. In addition to, or instead of, press fitting and/or snap fitting the blade cover to the blade portion of the main body, one or more fasteners may be used to secure the blade cover 232 to the main body. In the illustrative embodiment of FIG. 2, a screw 232*a* is used for securing the proximal end of the blade cover 232 to the main body 201.

As shown in FIG. 2, the handle 204 of the retractor houses therein a LED Driver Printed Circuit Board (PCB) 228, one or more power sources 230 configured to electrically connect to the LED Driver PCB 228, and at least a portion of the operating assembly 214, including a control flexible Printed Circuit Board (fPCB) 215. The LED Driver PCB 228 is configured to electrically connect the one or more power sources 230 with the LED flex circuit 213 via the connecting portion 213*a* of the LED flex circuit 213 and with the control fPCB 215 of the operating assembly via another connecting portion 215*a* so as to control power supply to the LED flex circuit 213 and to control the illumination assembly of the retractor. In FIG. 2, the LED Driver PCB 228 includes a central contact 228*a* protruding from its surface and configured to contact with terminals of the power sources, as well as peripheral contacts 228*b* configured to contact with opposing terminals of the power sources 230. When the LED Driver PCB 228 is positioned within the handle 204, the space between the LED Driver PCB 228 and the battery cover 234 covering the opening in the handle portion of the main body forms a battery compartment that accommodates the power sources 230 therein.

As mentioned above and shown in FIG. 2, the battery cover 234 is configured to cover the cavity within the main or central portion of the handle 204 that houses the LED Driver PCB 228 and accommodates the one or more power sources 230. The battery cover 234 may be fully removable from the main body 201 or may be partially removable from the main body 201 so as to open and close by hinging at one side in order to allow the one or more power sources to be removed and/or replaced. In the embodiment of FIG. 2, the battery cover 234, the LED driver PCB 228 and a push-tab 234*a* insertable into an opening within the battery cover 234 form a push-tab assembly described in U.S. Pat. No. 10,512,519, incorporated herein by reference. In the push-tab assembly, when the push-tab 234*a* is partially inserted into the opening within the battery cover 234, the push-tab 234*a* fits over the central contact 228*a* of the LED Driver PCB 228 such that electrically insulating legs of the push-tab 234*a* separate the battery terminals from the central contact 228*a*, thus electrically isolating the batteries from the central contact 228*a* of the LED Driver PCB 228. As a result, when the push-tab 234*a* is partially inserted into the opening in the battery cover 234, the power sources 230 are electrically isolated from the rest of the illumination assembly and power cannot be supplied to the other components of the illumination assembly even if the operating assembly 214 is operated to the ON state. This allows for safe shipping of the retractors with the batteries installed therein and without accidentally draining the batteries during shipment.

When the push-tab 234*a* of the push-tab assembly 234 fully inserted into the opening within the battery cover 234, the terminals of the batteries are allowed to electrically connect to the central contact 228*a* through openings within the legs of the push-tab 234*a*. Therefore, when the operating assembly 214 is operated to the ON state, the batteries can supply power to the illumination assembly. In this position of the push-tab 234*a*, the legs of the push-tab 234*a* engage with the battery terminals such that if the battery cover is opened or removed, the engagement between the legs of the push-tab 234*a* and the battery terminals pulls the batteries out of the battery compartment for a touch-free battery removal. Specifically, the batteries 230 can be removed from the handle of the retractor by opening or removing the battery cover 234 without touching the batteries and without risking contamination of the batteries with biohazardous materials.

The curved end portion 205 of the handle accommodates therein the operating assembly 214 for controlling the illumination assembly. The operating assembly 214 includes the control fPCB 215 and one or more operation members 214*a*, such as a button, a wheel, a slider or the like. The one or more operation members 214*a* are connected to or mounted on the control fPCB 215 and are used for controlling the ON/OFF state of the illumination assembly, the brightness and/or hue of the direct light sources and/or the direction of the light emission and/or angle(s) of the direct light sources relative to the blade surface. The curved end portion cover 235 couples to the distal end of the handle portion of the main body 201 so as to form the curved end portion 205. In the present illustrative embodiment, fasteners, such as screws 235*a*, are used to secure the curved end portion cover 235 to the main body 201. However, in other embodiments, the curved end portion cover 235 may be press-fit or snap-fit to the main body either instead of or in addition to using the fasteners or may be glued or otherwise attached to the main body. Other coupling methods may be used to connect the curved end portion cover 235 to the main body.

As shown in FIG. 2 and also visible in FIGS. 1A-1E, the control fPCB 215 of the operating assembly 214 is enclosed within the cavity between the main body and the curved end portion 205, and the one or more operation members 214*a* are provided on the curved end portion cover 235. In the illustrative embodiment of FIG. 2, the outer surface of the curved end portion cover 235 is concave and the one or more operation members 214*a* are provided on the concave surface of the curved end portion cover 235. In addition, the curved end portion cover 235 forms the suction port 222 configured to connect to a vacuum source.

As shown in FIG. 2, the curved end portion of the main body 201 is configured for attaching thereto the mounting adapter 220 configured to connect the retractor 200 to a fixed frame system or a fixed arm. Specifically, the mounting adapter 220 can be attached to the front surface of the curved end portion 205, which is opposite of the curved end portion cover 235 forming the rear surface and opposite of the operating assembly 214 a portion of which is exposed through the curved end portion cover 235. In the present illustrative embodiment, the mounting adapter 220 is releasably coupled or attached to the curved end portion 205 of the retractor 200. However, in other embodiments, the mounting adapter 220 may be permanently attached to the curved end portion 205 or may be integrated into the curved end so that the mounting adapter is integrally formed. Exemplary configurations of the mounting adapter 220 releasably attachable to the curved end portion 205 are described herein below with respect to FIGS. 3A-3I. FIGS. 3A, 3C, 3E, 3G and 3I show the mounting adapter 220 engaged and connected to the curved end portion 205, while FIGS. 3B, 3D, 3F and 3H show the mounting adapter 220 disengaged from and separated from the curved end portion 205.

As shown in FIGS. 3A-3I, the mounting adapter 220 is configured to engage with and releasably attach to the curved end portion 205 of the retractor handle. The curved end portion 205 includes a cavity or recess 302 formed therein configured to receive a portion of the mounting adapter 220. This portion of the mounting adapter 220 can engage with the recess 302 when inserted therein and can lock or be secured to the curved end portion 205 so as to prevent disengagement of the mounting adapter 220. The mounting adapter 220 includes a connector tip 321 configured to engage with and connect to a fixed frame system or a fixed arm for holding and positioning the retractor. The connector tip 321 in the illustrative embodiment of FIGS. 3A-3I comprises a post that is configured to quickly and easily connect to a Quick connect hex fitting on a fixed frame or fixed arm. However, other types of connector tips, including tips that can connect to other standard fittings, may be used in the mounting adapter 220, and in some embodiments, different mounting adapters 220 with different types of connector tips may be used with the retractor 200 of the present invention. This configuration, in which the mounting adapter is releasably attached to the retractor and different mounting adapters are used to allow for different types of connections, provides the user with additional flexibility in using the retractor 200 as a hand-held retractor as well as a fixed frame retractor with different types of fixed frames or fixed arms.

The mounting adapter 220 of the present invention includes a coupling extension 322 sized and shaped to be inserted into and to fit within the recess 302 formed in the curved end portion 205. In order to ensure secure fit and to avoid movement of the mounting adapter 220 relative to the curved end portion 205, the shape of the coupling extension 322 in the illustrative embodiment of FIGS. 3A-3B conforms to an internal shape of the recess. In some embodiments, the coupling extension 322 has a substantially cylindrical shape and may have a tapering distal end. In some embodiments, the coupling extension 322 may have a parallelepiped shape, a cube shape, a cone shape, a pyramid shape, an obelisk shape, an ellipsoid shape, or any other suitable shape that conforms substantially to the shape of the cavity/recess 302 in the curved end portion 205. In the illustrative embodiment of FIGS. 3A-3I, the coupling extension 322 has semi cylindrical or semi ellipsoid shape with a rounded elongated surface 322*a* and an opposing substantially flat surface 322*b*. The distal end of the exemplary coupling extension 322 in FIGS. 3A-3I is truncated so as to have a substantially flat tip 322*c*. A proximal end of the coupling extension 322 comprises a portion having a greater thickness than the rest of the coupling extension 322 extending from the substantially flat surface 322*b*. This shape of the coupling extension 322 limits the size and thickness of the coupling extension and prevents rotational and lateral movement of the mounting adapter 220 relative to the curved end portion 205 when the coupling extension 322 is engaged with the recess 302. In addition, with this shape of the coupling extension, the substantially flat surface 322*b* abuts an inside surface of a substantially flat outer wall portion of the curved end portion which allows for secure fastening using a screw fastener, as described below.

Figure 3A:
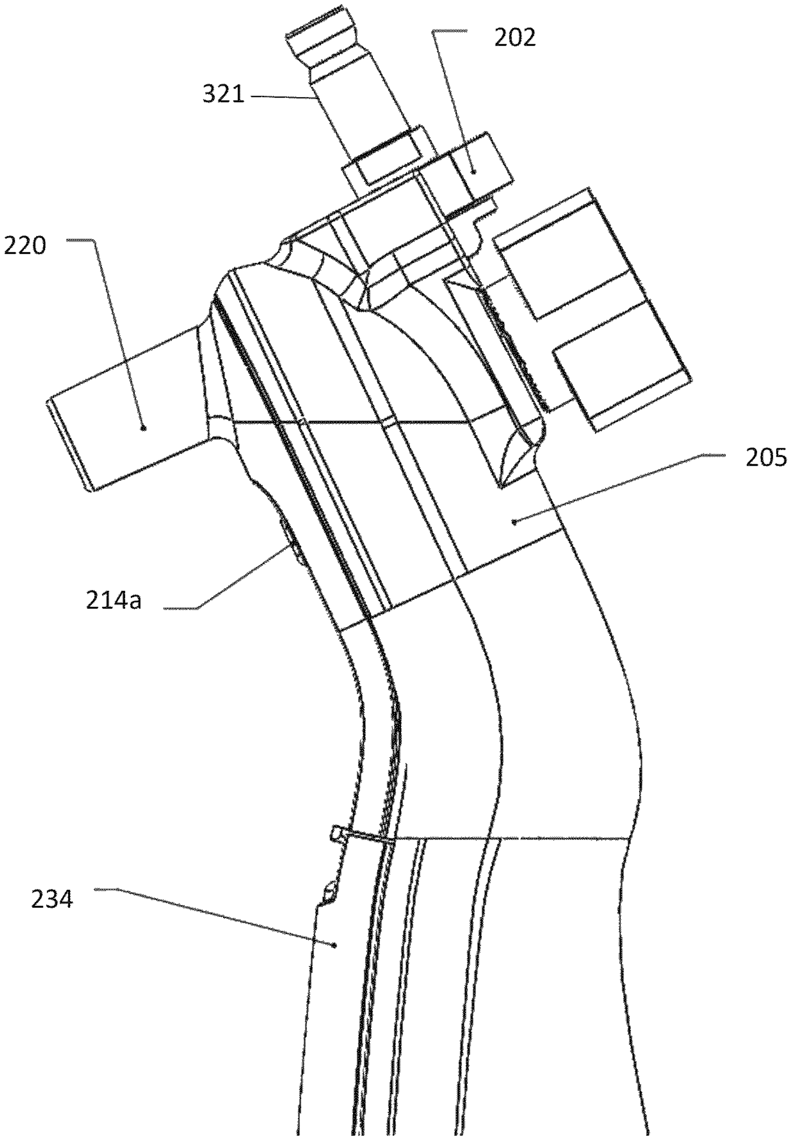
FIG. 3A shows an enlarged side view of a distal curved end portion of a handle of the surgical retractor of FIGS. 1A-1E.
Figure 3B:
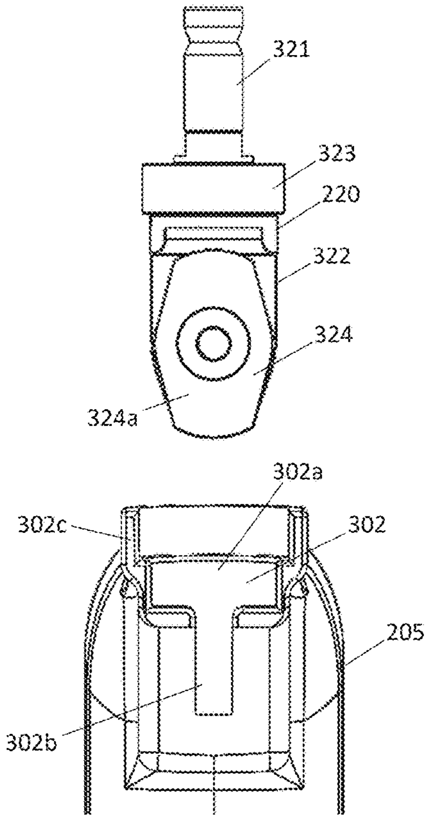
FIGS. 3B, 3D, 3F and 3H shows other enlarged views of the distal curved end portion of a handle of the surgical retractor with a fixed frame mounting adapter detached from the handle.
Figure 3D:
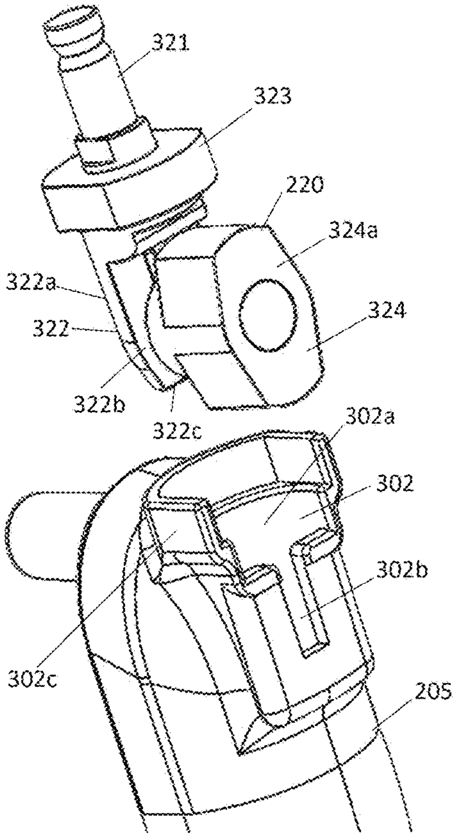
Figure 3C:
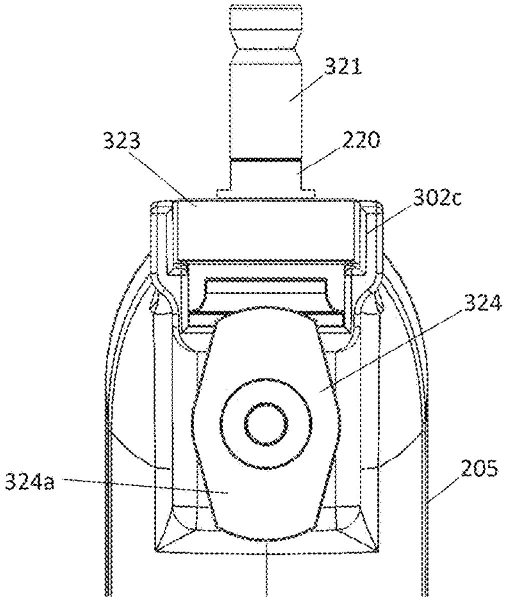
FIGS. 3C, 3E, 3G and 3I show corresponding views of the distal curved end portion of the handle with the fixed frame mounting adapter attached thereto.
Figure 3E:
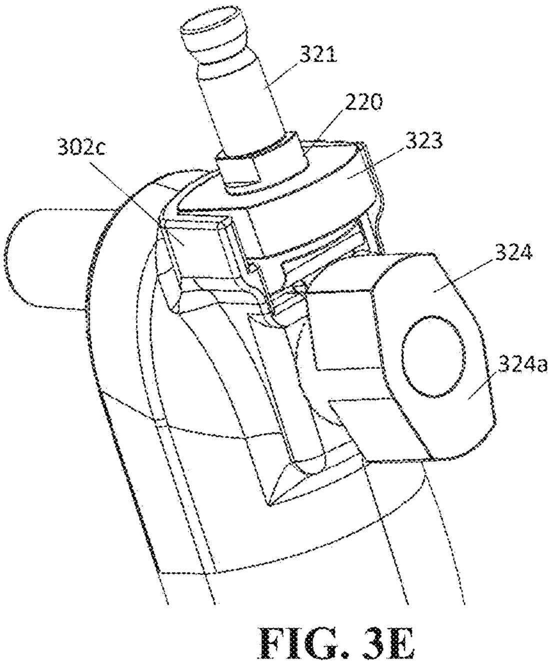
Figure 3F:
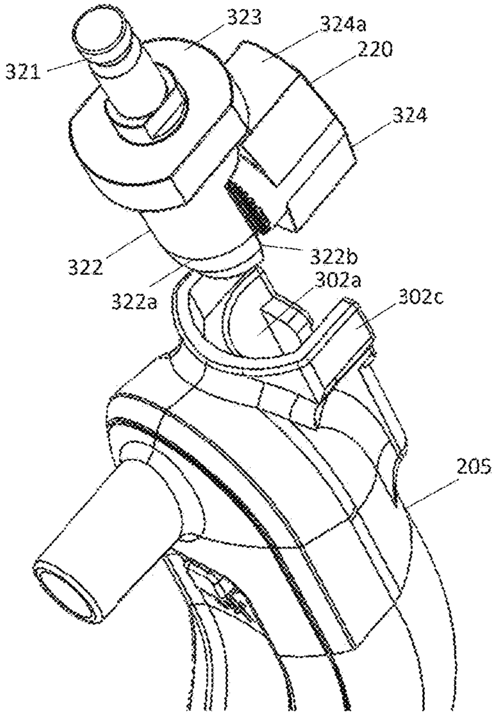
Figure 3G:
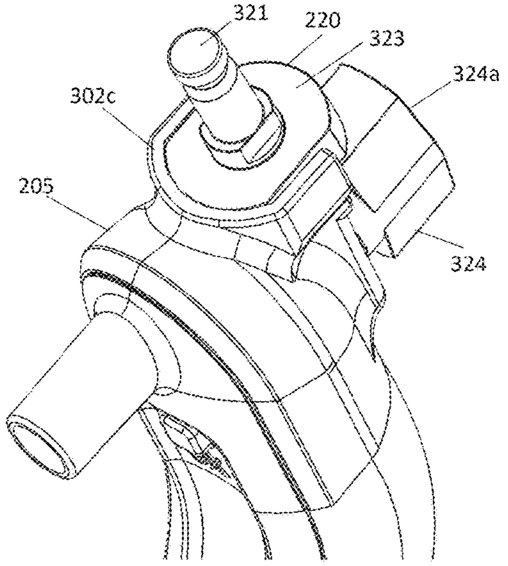
Figure 3H:
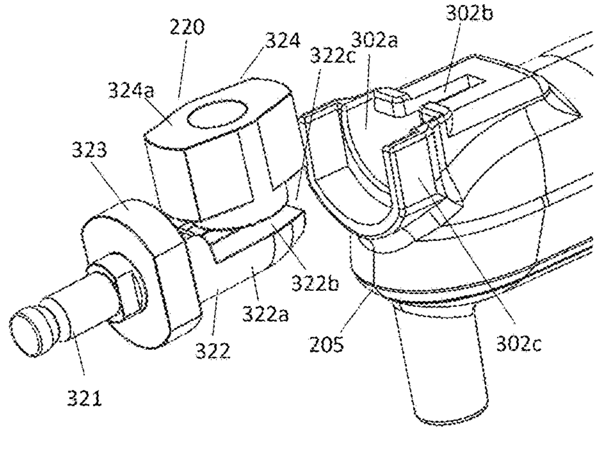
Figure 3I:
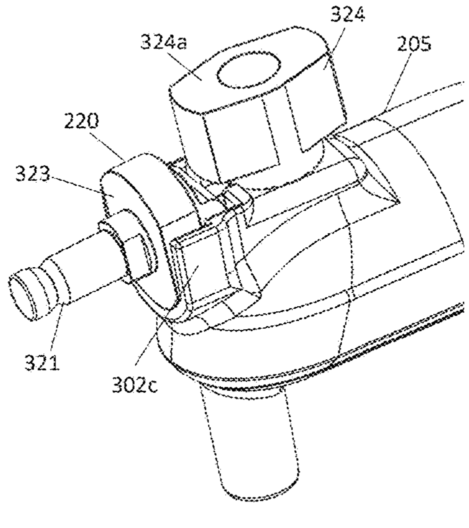

In addition, in the illustrative embodiment of FIGS. 3A-3I, the mounting adapter 220 also includes a collar or flange 323 provided between the connector tip 321 and the coupling extension 322, and a fastener 324, such as a screw, a clamp, a bolt tensioner, or other suitable fastening device, for securing the adapter to the curved end portion 205. The flange 323 may comprise an annulet extending around the entire circumference of the mounting adapter 220, having a rounded or an oval shape, as can be seen in FIGS. 3F and 3H. In some embodiments, the flange may have a square, a rectangular or a triangular cross-section or an irregularly shaped cross-section. In other embodiments, the flange 323 may extend around a portion or multiple portions of the circumference of the mounting adapter 220. The flange 323 forms a boundary wall between the coupling extension 322 from the connector tip 321 and separates the coupling extension 322 from the connector tip 321.

The fastener 324 in the illustrative embodiment comprises a screw fastener extending from the substantially flat surface 322*b* of the coupling extension 322. The fastener includes a post or shank (not visible) which extends from the coupling extension 322 and can be screwed into the thickness of the coupling extension 322, and a head 324*a* which can be turned to screw the fastener 324 into the coupling extension 322 or out of the coupling extension 322. In other embodiments, other types of fasteners 324, including clamps, bolt tensioners and other means of attachment or securement, may be used to secure the mounting adapter 220 to the curved end portion 205 of the retractor.

As can be seen in FIGS. 3A-3I, the recess 302 formed in the curved end portion 205 of the handle has an opening 302*a* at or near the distal tip of the curved end portion 205 and the recess 302 extends into the curved end portion 205 in a direction toward the main portion of the handle 204. The recess 302 is formed in the main body 201 of the retractor, on a side of the curved portion that is opposite of the curved end cover side where the suction port 222 and the operation member 214*a* are provided. As discussed above, the recess 302 is shaped to receive the coupling extension 322 of the mounting adapter 320 by sliding the coupling extension 322 into the recess 302 through the opening 302*a*.

As shown in FIGS. 3B, 3D and 3H, an exterior wall of the curved end portion 205 includes an elongated slot 302*b* therein that extends from the opening 302*a* of the recess 302 and along a portion of the length of the recess 302. The width of the elongated slot 302*b* is narrower than the width of the opening 302*a*. The elongated slot 302*b* is sized to receive the shank of the screw fastener 324 so that when the coupling extension 322 is inserted into the recess 302 through the opening 302*a*, the shank of the screw fastener 324 slides into the slot 302*b*, while the head 324*a* remains outside of the recess 322. Both the coupling extension 322 and the head 324*a* of the screw fastener 324 are larger than the width of the elongated slot 302*b* so that when the screw fastener 324 is turned to secure the mounting adapter 320 to the curved end portion, the exterior wall of the curved end portion around and adjacent to the elongated slot 302*b* is sandwiched between the head 324*a* of the screw fastener 324 and the substantially flat surface 322*b* of the coupling extension 322.

In the illustrative embodiment of FIGS. 3A-3I, the curved end portion 205 includes a sidewall extension 302*c* that extends from the periphery of the recess opening 302*a* or extends adjacent to the periphery of the recess opening 302*a*. The sidewall 302*c* extends around at least a portion of the circumference of the recess opening 302*a* and forms a sleeve for accommodating and at least partially surrounding the flange 323 of the mounting adapter 320. As can be seen in FIGS. 3B-3I, when the mounting adapter is fully inserted into the recess 322 and secured to the curved end portion 205, the sidewall 302*c* extends around a portion of the flange 323 so as to cradle the flange. With this configuration, the shape of the recess 302 and the surrounding sidewall 302*c* prevent rotational and lateral movement of the mounting adapter 320 relative to the curved end portion 205 and assist in securing the mounting adapter 320 to the curved end portion 205.

The above-described configurations of the retractor handle, and in particular, of the curved end portion of the handle, and the mounting adapter, allow the retractor to be used as a hand-held retractor, with or without the mounting adapter attached to the handle, and to be easily connected to and disconnected from a fixed frame or a fixed arm of a stationary positioning system/surgical positioning device. The placement of the mounting adapter on the curved end portion 205 of the retractor prevents interference of the mounting adapter with the operator's grip during hand-held use of the retractor and also provides for a desirable positioning and orientation of the retractor when the mounting adapter is attached to a fixed frame or a fixed arm. Although the embodiments described above include a mounting adapter on the curved portion 205 of the retractor handle, it is contemplated that the configuration of the retractor may be modified so as to provide the mounting adapter in a different area of the handle or even at the curved joint portion of the retractor. Such modifications, however, would need to ensure that the mounting adapter and/or the attachment mechanism for the mounting adapter do not impede the user's ability to comfortably hold the retractor during hand-held operation and do not obstruct the user's view of the target operating site during use.

As discussed above, the retractor of the present invention can be used for soft tissue retraction as well as for vein retraction and for cradling a vein, and the blade of the retractor includes an atraumatic curved tip. FIGS. 4A and 4B-4C show two embodiments of the atraumatic curved tip of the blade. The atraumatic curved tip shown in FIG. 4A corresponds to the blade tip of the retractor shown in FIGS. 1A-2.

Figure 4A:
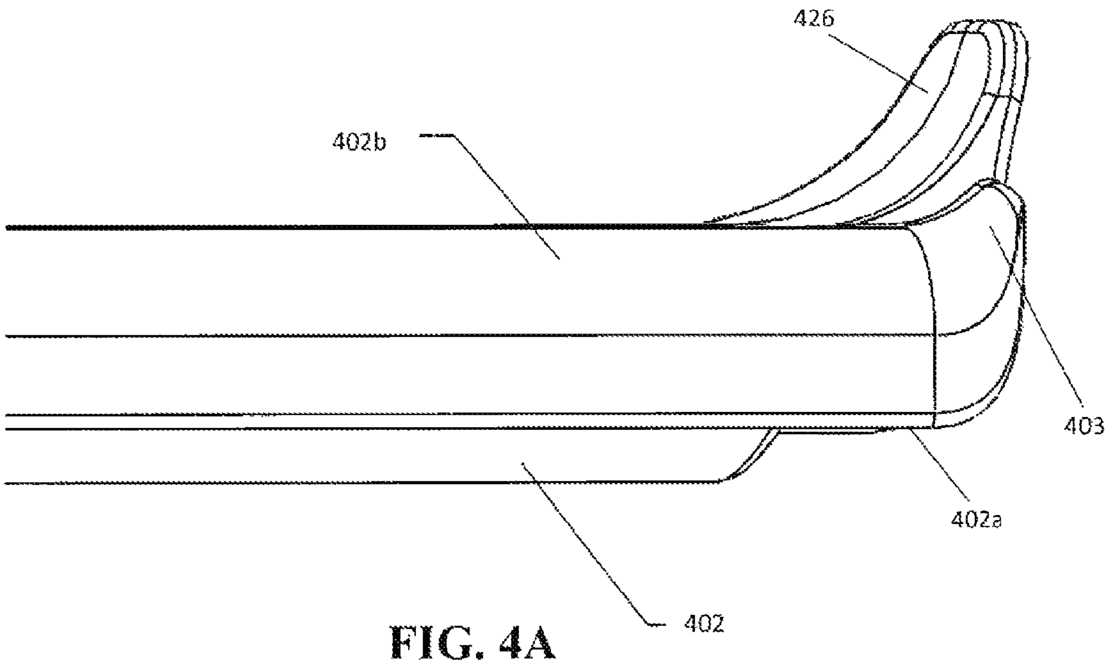
FIG. 4A shows one embodiment of the distal end portion of the blade of the surgical retractor.

As shown in FIG. 4A and also visible in FIGS. 1B and 1E, the distal end of the blade 402/102 curves slightly to form a curved lip 403. The curved lip 403 curves in a direction away from the bottom surface 402*a* of the blade 402. In some embodiments, the curved lip 403 of the blade has substantially the same width as the remaining portion of the blade 402. In other embodiments, including those shown in FIGS. 1B, 1E and 4A, the curved lip 403 has curved corners which gradually taper the width of the curved lip relative to the width of the remaining portion of the blade 402. In addition, as shown in FIGS. 1B, 1E and 4A, the distal end of the blade 402, 102 also includes an atraumatic curved tip 426/126 extending or protruding from the top surface 402*b* of the distal end of the blade 402 along or abutting the curved lip 403 at the distal end. The atraumatic curved tip 426 has a smooth top surface in the present embodiment. However, in other embodiments, limited gripping surface may be used on the atraumatic curved tip 426, depending on the intended application of the retractor.

The atraumatic curved tip 426/126 gradually extends along the top surface of the curved lip 403 and extends beyond the curved lip 403. In the embodiments shown in FIGS. 1B, 1E and 4A, the width of the atraumatic curved tip 426/126 is smaller than the width of the curved lip 403 and the remaining portion of the blade 402, and the width of the atraumatic curved tip 426/126 gradually tapers from an attached end of the tip 426/126 to its free distal end. In certain embodiments, the width of the attached end of the atraumatic curved tip 426/126 is between ½ and ¾ of the blade width, and preferably between ½ and ⅔ of the blade width, while a width of the free distal end of the atraumatic curved tip 426/126 is ⅔ of the blade width or smaller and in some embodiments ½ of the blade width or smaller. The smaller width of the atraumatic curved tip 426/126 relative to the width of the blade allows the atraumatic curved tip 416/126 to engage with a vein and to cradle a vein and/or provide vein retraction. At the same time, the above-described configuration of the distal end of the blade allows the retractor to be used for soft tissue retraction, thus providing flexibility and multiple uses of the retractor of the present invention.

Figure 4B:
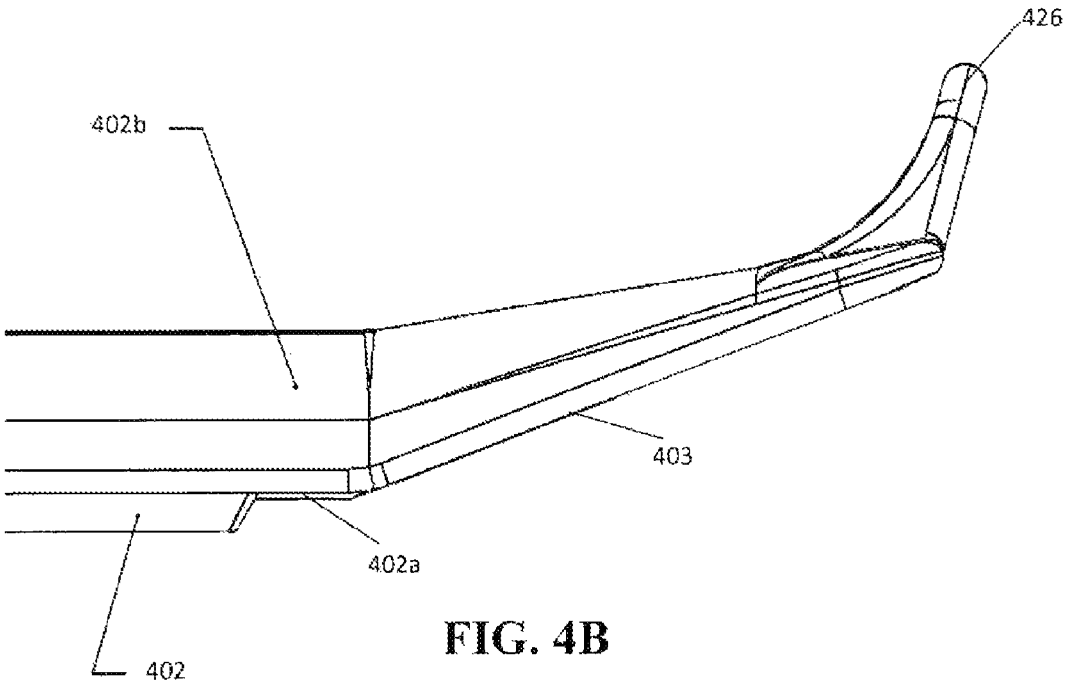
FIGS. 4B-4C show another embodiment of the distal end portion of the blade of the surgical retractor.
Figure 4C:
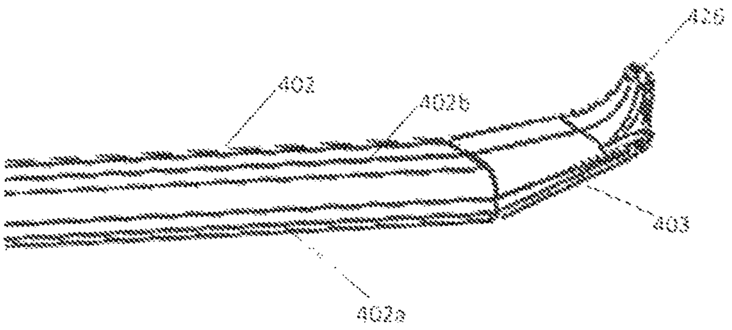

FIGS. 4B-4C show a second embodiment of the distal end of the blade 402 with the atraumatic curved tip 426. As shown in FIGS. 4B and 4C, the distal end of the blade has an angled end 403 which is angled in a direction away from the bottom surface 402*a* and tapers in thickness and width in a direction of a distal tip of the blade 402. The top surface 402*b* of the angled end 403 in FIGS. 4B-4C is slightly angled relative to the top surface of the rest of the blade 402, while the bottom surface 402*a* of the angled end 403 is angled at a larger angle than the top surface 402*b* thereof due to the tapering of the angled end 403 in the thickness direction. As shown in FIGS. 4B-4C, the atraumatic curved tip 426 extends from the top surface 402*b* of the angled end 403 and forms a curved distal tip of the blade 402. The curvature of the atraumatic curved tip 426 forms a concave top surface of the tip and in some embodiments, forms a hook-shaped tip. The top surface of the atraumatic curved tip 426 is smooth in the present embodiment, but in certain embodiments, a gripping surface may be provided on the top surface of the atraumatic curved tip 426, depending on the intended applications of the retractor. As in the first embodiment of FIG. 4A, the atraumatic curved tip 426 in the second embodiment can be used for soft tissue retraction as well as to provide minimal vein retraction and to cradle a vein without causing trauma to the vein.

Figure 5:
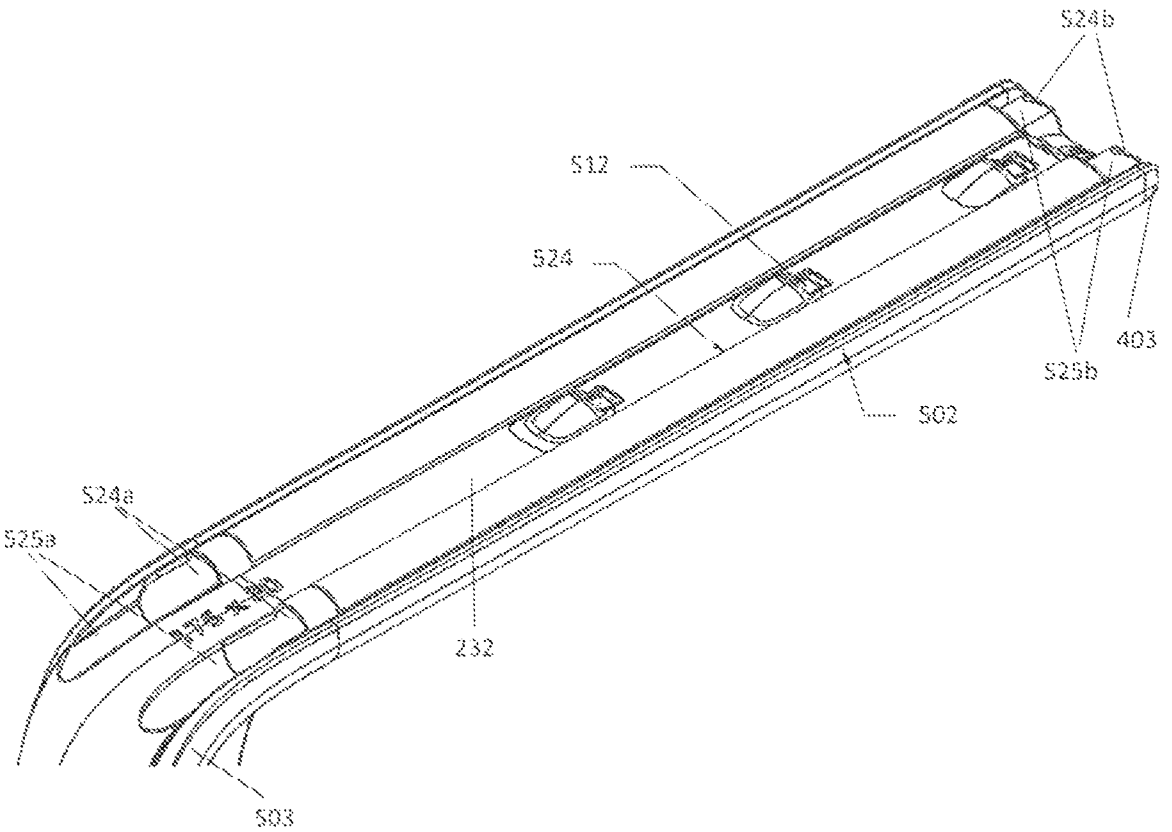
FIG. 5 shows an enlarged view of the blade and a portion of the handle of the surgical retractor.

Although FIGS. 4A-4C show two embodiments of the atraumatic curved tip 426, the configurations of the distal end of the blade may be modified without detracting from the above-described functionalities of the retractor. Specifically, the overall configuration of the distal end of the blade may be modified and may still include an atraumatic curved tip that has a gradual curvature of the top surface and/or a hook-like shape, and the top surface of the atraumatic curved tip is smooth so as to reduce or eliminate likelihood of trauma to a vein and/or soft tissues. Also, the atraumatic curved tip of such modified embodiment preferably tapers toward the distal tip of the blade to enable the curved tip to hook under a vein and to cradle the vein. As shown in FIGS. 1A-1E and described above, the blade 102 of the retractor also includes one or more elongated channels 124 extending along its bottom surface 102*a*. The channels are formed on the blade cover 232 and extend along the majority of the length of the blade. FIG. 5 shows the blade 502 of the retractor in more detail with two elongated channels 524 extending along each side of the blade along the majority of the length of the blade 502.

In the illustrative embodiment shown in FIG. 5, each channel 524 extends from the proximal end of the blade 502 or from the curved joint 503 to the distal end of the blade 502, ending at or before the curved lip 403 of the blade 502. Each channel 524 forms an enclosed passageway between an open proximal end 524*a* and an open distal end 524*b*. In the embodiment of FIG. 5, the one or more direct light sources 512 of the illumination assembly are positioned substantially centrally along the length of the blade, and the channels 524 in FIG. 5 extend on either side of the central portion of the blade cover that accommodates the direct light sources 512. With this configuration, the illumination assembly provides sufficient lighting to the surgical pocket and the channels do not interfere or obstruct a user's view of the surgical pocket.

The channels 524 are configured to allow insertion of surgical instruments, hardware and equipment for access to the surgical site. For example, the channels 524 may allow for insertion of an endoscope or similar visualization device to allow for observation of the surgical site or for insertion of cannula or similar devices to drain fluids, administer medications or provide irrigation to the surgical site. Moreover, the retractor of the present invention shown in FIGS. 1-5 can be used for spinal surgeries or other orthopedic surgeries. Specifically, during spinal or other orthopedic surgeries, hardware can be inserted through one or both channels 524 on the blade to position and retain the retractor blade position relative to the bone while also retracting a vein using the above-described atraumatic curved tip on the blade. The retractor can also be attached to a fixed frame or fixed arm using the mounting adapter described above. Thus, the retractor of the present invention has the flexibility of being used as a soft tissue retractor and as a spine or orthopedic retractor. In addition, due to the positioning of the channels along each side of the cover, any instruments, hardware or equipment inserted into the channels does not interfere with or obstruct illumination provided by the centrally located direct light sources 512 and does not obstruct a user's view of the surgical pocket.

Although in FIGS. 1A-1E and 5, the channels extend from the proximal end of the blade to the distal end of the blade, in other embodiments, the channels 524 may be shorter in length as long as they provide sufficient enclosure and stability for instruments that may be inserted therein.

As mentioned herein above, the channels 524 are formed in the blade cover 232 of the retractor, with the blade cover extending from the blade to a portion of the handle. With this configuration, when hardware is inserted into the channels 524, any loads on the hardware are absorbed by the handle of the retractor and the main body of the retractor, and the blade cover acts only as a guide for the hardware inserted into the channels.

Moreover, as shown in FIG. 5, each channel 524 is at least partially embedded into the blade so that an inner surface of the channel 524 is positioned closer to the interior of the blade and closer to the top surface of the blade than surrounding external surfaces of the blade cover 232. For example, the outer surface of the blade cover 232 between the two channels 524, which accommodates the one or more direct light sources 512, is positioned further away from the opposing top surface of the blade than an inner concave surface of each channel 524. Moreover, the outer surface of each channel 524 forming part of the bottom surface of the blade cover 232 is positioned further away from the opposing top surface of the blade than the outer surface of the blade cover 232 between the two channels 524 and forms a convex surface. This configuration reduces the profile of the blade so that the channels 524 do not protrude extensively from the blade cover 232 and do not interfere with the view of a surgical site.

In the illustrative embodiment of FIG. 5, the proximal end of each channel 524 includes an open or uncovered portion 525*a* which is used to guide any hardware or equipment into the channel 524. In addition, the distal end of each channel 524 includes a sleeve 525*b* with a smaller cross-section extending from the distal end of the channel. The sleeves

525*b* extend the length of the channels 524 and help position the hardware, instruments and equipment within the channels.

Moreover, when smoke evacuation is needed during a surgical procedure, the channels 524 may be adapted to provide smoke evacuation within a surgical pocket by attaching a smoke evacuation adapter (not shown) to the proximal ends of the channels. The smoke evacuation adapter is configured to fluidly couple the proximal end 524*a* of one or more of the channels 524 with the handle and with the suction port 122 in the handle of the retractor. In some embodiments, the blade cover 232 includes an opening at or near the proximal end of each channel, such as in the uncovered portion 525*a* of each channel 524 that provides access into the handle of the retractor. In some embodiments, the smoke evacuation adapter includes a pair of tubes, each configured to have one end inserted into each channel 524 via the openings 524*a* and an opposing end inserted into the corresponding opening in the blade cover 232. In other embodiments, the smoke evacuation adapter may be used to couple the proximal end 524*a* of one or more of the channels 524 directly with a suction source, rather than coupling the one or more channels 524 with the handle of the retractor. An exemplary embodiment of such a smoke evacuation adapter 627 used with the retractor of the present invention is shown in FIG. 6 described herein below.

Although in the present illustrative embodiment of FIG. 5, two channels 524 are provided on the retractor blade, in some embodiments, only one channel 524 may be used. In yet other embodiments, one channel 524 with open proximal and distal ends is included for insertion of instruments, hardware and equipment therethrough, while the other channel 524 is fluidly coupled to the handle and to the suction portion 122 in order to provide smoke evacuation therethrough.

Figure 6:
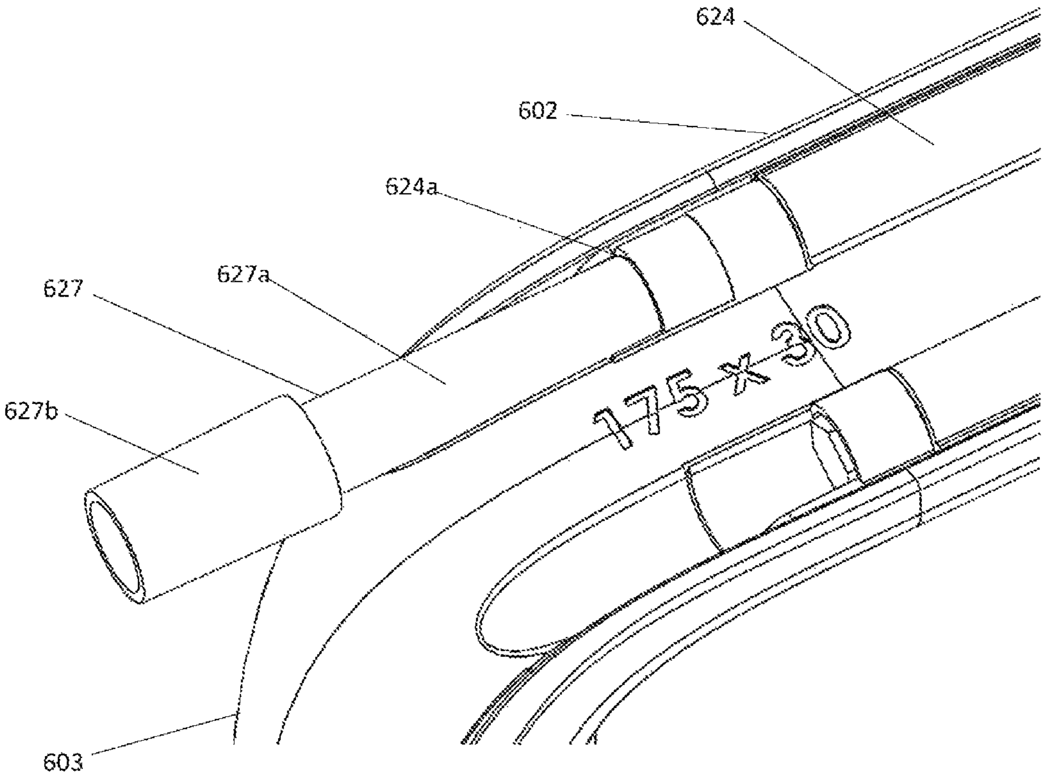
FIG. 6 shows a proximal portion of the blade with an illustrative smoke evacuation adapter inserted into one of the channels on the blade.

FIG. 6 shows a proximal end portion of the blade 602 and curved joint 603 of the retractor with an exemplary smoke evacuation adapter 627 coupled to the proximal end 624*a* of one of the channels 624. As shown, the smoke evacuation adapter 627 includes a tube 627*a*, which can have a cylindrical cross-section or any other suitable cross-section, and a port connector 627*b* at the proximal end of the tube 627*a*. The tube 627*a* is inserted into one of the channels 624 provided on the blade so as to fluidly couple the channel 624 with a suction source. In certain embodiments, the tube 627*a* extends from the connector 627*b* and ends at or slightly beyond the connection point with the proximal end 624*a* of the channel 624. In other embodiments, the tube 627*a* extends through the channel 624 and along a portion of the length of the channel 624, while in yet other embodiments, the tube 627 extends through the full length of the channel 624. The tube 627*a* is attached to the channel 624 using any suitable method, such as press-fitted into the channel as shown in FIG. 6, screwed into the channel 624, snap-fitted into the channel, or using any other attachment method. In addition, although the tube 627*a* is shown as being linear or substantially linear in shape in FIG. 6, in other embodiments, the tube may be angled, jagged, curved or any other suitable shape. In the embodiment of FIG. 6, the smoke evacuation adapter 627 is configured to directly connect to a vacuum source via the port connector 627*b*. However, in other embodiments, the smoke evacuation adapter 627 may omit the port connector 627*b* and may instead be fluidly connected to the handle and to the port formed in the handle.

Figure 7A:
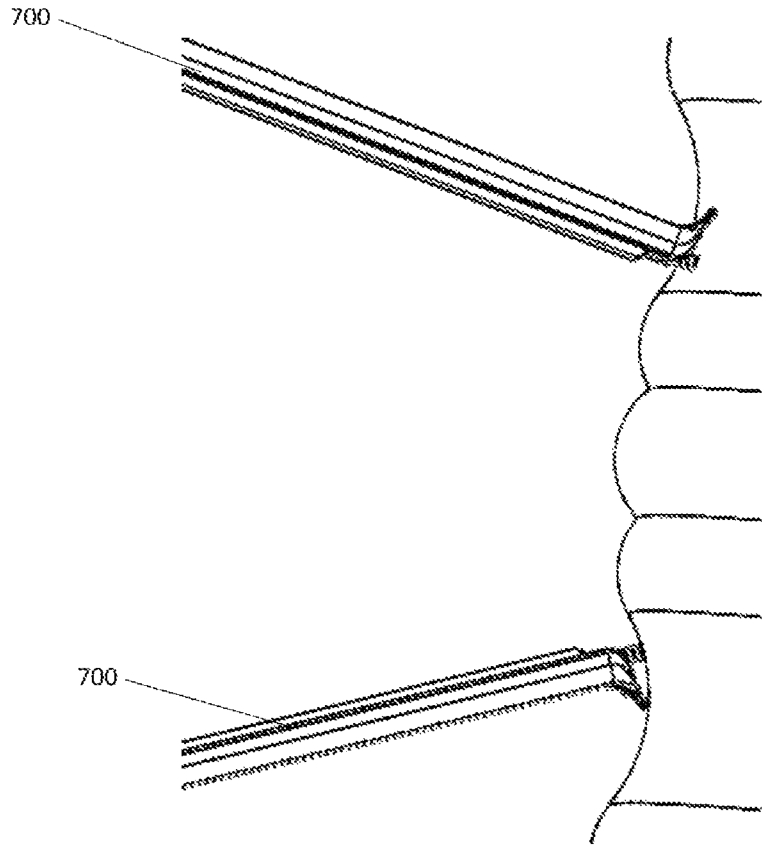
FIGS. 7A-7C demonstrate use of the surgical retractor of the present invention during spinal surgeries.
Figure 7B:
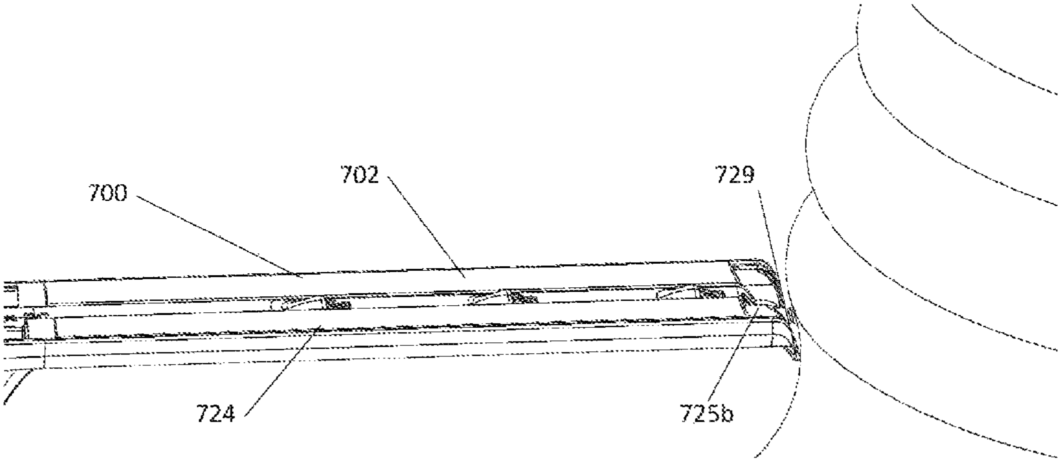
Figure 7C:
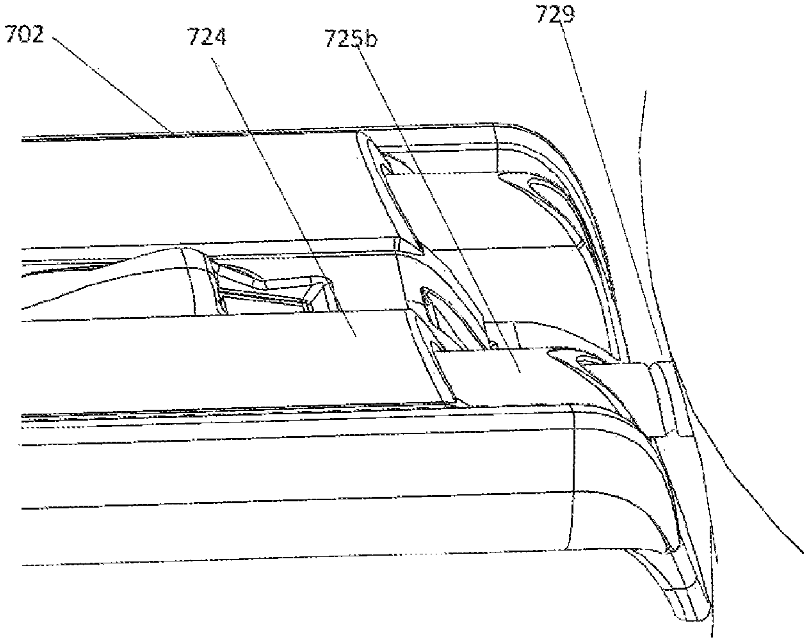

As mentioned above, the channels on the blade of the retractor can be used for insertion of instruments and enable the retractor of the present invention to be used in spinal and orthopedic applications. FIGS. 7A-C illustrate use of the retractor(s) of the present invention during spinal surgery, wherein the retractor(s) 700 is secured to the bone. FIG. 7A shows a portion of a spine with two retractors 700 of the present invention secured to vertebrae of the spine. The retractors 700 may be used for retracting soft tissues and one or more veins, and/or for stabilizing the vertebrae during spinal surgical procedures. As shown in FIG. 7A and as more clearly visible in the enlarged views of FIGS. 7B and 7C, a long shaft or screw 729 with a threaded end is passed through the channel 724 on the blade 702 of the retractor. The threaded end of the shaft extends externally from an opening in the sleeve 725*b* at the distal end of the channel 724. After the retractor 700 is positioned relative to the respective vertebra, the threaded end of the shaft or screw is screwed into the vertebra so as to secure the position of the retractor 700 relative to the spine. Due to the length of the channel and the construction of the retractor with the channels on the blade, the retractor remains securely in place after the screw is secured to the vertebra and any loads on the blade and on the channel are absorbed by the handle of the retractor. In addition, the angle of the atraumatic tip of the blade allows it to rest against the vertebra, as shown in FIG. 7C, providing additional stability to the retractor secured to the spine.

As described above, the retractor of the present invention is configured for multiple different uses, including hand-held use or being mounted on a fixed frame or fixed arm, and including use for soft tissue retraction, vein retraction and spinal or orthopedic applications. This flexibility provides significant cost savings by eliminating the need to purchase and keep in stock multiple types of retractors for different applications. Moreover, these features and flexibility of the present retractor increases efficiencies during surgical preparation which require surgical staff to provide all necessary equipment needed for surgery in advance.

While various features and variations thereof have been described with respect to retractors, it is noted that one or more of the features described herein may be embodied within other medical devices. The specific configurations of the LED arrangement, channel configuration and positioning, mounting adapter configuration and attachment to the device, etc. may be modified, as needed, for the specific device in which is it used.

In all cases, it is understood that the above-described arrangements are merely illustrative of the many possible specific embodiments which represent applications of the present invention. Numerous and varied other arrangements, including use of different materials and various configurations of components of the retractor, can be readily devised without departing from the spirit and scope of the invention.

We claim:

1. A surgical retractor, comprising:
a handle;
a blade extending from the handle; and
a mounting adapter configured to releasably engage with the handle,
wherein the handle has an ergonomic construction configured for hand-held use of the retractor,
wherein the handle includes a recess configured to receive a portion of the mounting adapter so as to engage with the mounting adapter,
wherein the mounting adapter is configured to directly attach to a fixed arm of a surgical positioning device,
wherein the handle includes a main portion and a curved distal end portion that provides the recess, wherein the blade extends substantially perpendicularly from a longitudinal axis of the main portion in a first direction and the curved distal end portion extends at an acute angle from the longitudinal axis of the main portion in a second direction opposite of the first direction, and wherein the handle is configured such that when the mounting adapter is engaged with the handle, the mounting adapter is oriented substantially parallel to a longitudinal axis of the curved distal end portion.

2. The surgical retractor in accordance with claim 1, wherein the handle has a hollow construction.

3. The surgical retractor in accordance with claim 2, further comprising an illumination assembly including at least one direct light source provided on the blade, and one or more electrical components housed in the handle.

4. The surgical retractor in accordance with claim 3, wherein the illumination assembly includes one or more power sources housed in the handle.

5. The surgical retractor in accordance with claim 1, wherein the mounting adapter is integrated into the curved distal end portion of the handle.

6. The surgical retractor in accordance with claim 1, wherein the handle is configured to releasably engage with the mounting adapter, wherein the mounting adapter is configured to directly attach to the fixed arm and is further is configured to selectively attach to different fixed arms.

7. The surgical retractor in accordance with claim 1, wherein the handle includes a first surface, at least a portion of the first surface facing in the first direction, and a second opposing surface, and wherein the mounting adapter is provided on the first surface of the curved distal end portion.

8. The surgical retractor in accordance with claim 1, wherein the curved distal end portion is configured to releasably engage with the mounting adapter.

9. The surgical retractor in accordance with claim 8, wherein the mounting adapter includes a connector tip configured to attach to a corresponding connector of the fixed arm and a coupling extension configured to engage with the recess in the curved distal end portion of the handle.

10. The surgical retractor in accordance with claim 9, wherein a shape of the coupling extension corresponds to a shape of the recess in the curved distal end portion of the handle.

11. The surgical retractor in accordance with claim 10, wherein the mounting adapter further includes a fastener for securing the engagement between the coupling extension and the recess in the curved distal end portion when the coupling extension is inserted into the recess.

12. The surgical retractor in accordance with claim 1, wherein the blade includes at least one channel therein, the at least one channel forming an enclosed passage between a first opening adjacent a proximal end portion of the blade and a second opening adjacent a distal end portion of the blade.

13. The surgical retractor in accordance with claim 12, wherein the at least one channel is configured to allow insertion of one or more instruments therethrough.

14. The surgical retractor in accordance with claim 12, wherein the at least one channel is partially embedded into a thickness of the blade.

15. The surgical retractor in accordance with claim 12, wherein the at least one channel extends along a majority of a length of the blade.

16. The surgical retractor in accordance with claim 12, wherein the at least one channel includes a first channel extending adjacent a first side of the blade and a second channel extending adjacent a second side of the blade.

17. The surgical retractor in accordance with claim 16, further comprising an illumination assembly including at least one direct light source provided on the blade, wherein the at least one direct light source is provided between the first and second channels.

18. The surgical retractor in accordance with claim 12, further comprising a smoke evacuation adapter configured to releasably connect to the at least one channel and to fluidly connect the at least one channel to a suction source.

19. The surgical retractor in accordance with claim 1, wherein the blade includes an atraumatic curved tip extending from a distal end portion of the blade and configured to provide soft tissue retraction and vein retraction.

20. The surgical retractor in accordance with claim 19, wherein the atraumatic curved tip tapers toward a distal tip of the blade.

21. The surgical retractor in accordance with claim 19, wherein a proximal end of the atraumatic curved tip attached to the distal end portion of the blade has a smaller width than the rest of the distal end portion.

22. The surgical retractor in accordance with claim 1, wherein the mounting adapter includes a coupling portion configured to engage with the handle and a connector tip configured to directly attach to a corresponding connector of the fixed arm.

23. The surgical retractor in accordance with claim 1, wherein the mounting adapter is interchangeable with other mounting adapters configured to directly attach to different connectors of fixed arms.

24. The surgical retractor in accordance with claim 1, wherein the handle defines a concave surface that is configured to prevent hand slippage along the handle, and wherein the concave surface and the mounting adapter are positioned along a same side of handle.

25. A spinal surgical assembly comprising:

a surgical retractor comprising a handle and a blade extending from the handle; and a screw comprising a shaft and a threaded end, wherein the handle of the surgical retractor has an ergonomic construction configured for hand-held use of the retractor, and the handle is further configured to attach to one or more of a fixed frame and a fixed arm of a surgical positioning device, wherein the blade includes at least one channel therein, the at least one channel forming an enclosed passage between a first opening adjacent a proximal end portion of the blade and a second opening adjacent a distal end portion of the blade, and wherein the screw is configured to pass through the at least one channel such that the threaded end extends from the second opening in the at least one channel and to secure the surgical retractor to a bone or a vertebra.

26. A surgical retractor comprising:

a handle;

a blade extending from the handle;

a mounting adapter configured to releasably engage with the handle; and an illumination assembly including at least one direct light source provided on the blade, and one or more electrical components housed in the handle, wherein the handle has an ergonomic construction configured for hand-held use of the retractor, wherein the handle is further configured to attach to one or more of a fixed frame and a fixed arm of a surgical positioning device via the mounting adapter, wherein the handle includes a main portion and a curved distal end portion, wherein the blade extends substantially perpendicularly from a longitudinal axis of the main portion in a first direction and the curved distal end portion extends at an acute angle from the longitudinal axis of the main portion in a second direction opposite of the first direction, and wherein the handle is configured such that when the mounting adapter is engaged with the handle, the mounting adapter is oriented substantially parallel to a longitudinal axis of the curved distal end portion.

27. The surgical retractor in accordance with claim 26, wherein the mounting adapter is configured to selectively attach to the one or more of a fixed frame and a fixed arm of a surgical positioning device.

28. The surgical retractor in accordance with claim 27, wherein the mounting adapter includes a coupling portion configured to engage with the handle and a connector tip configured to directly attach to a corresponding connector of the one or more of a fixed frame and a fixed arm of a surgical positioning device.

29. The surgical retractor in accordance with claim 26, wherein the distal end portion of the handle is configured to attach to the one or more of a fixed frame and a fixed arm of a surgical positioning device via the mounting adapter.

30. The surgical retractor in accordance with claim 26, wherein the handle defines a concave surface that is configured to prevent hand slippage along the handle, and wherein the concave surface and the mounting adapter are positioned along a same side of handle.

* * * * *